(12) United States Patent
Maebashi et al.

(10) Patent No.: US 9,851,329 B2
(45) Date of Patent: Dec. 26, 2017

(54) ANALYTICAL CELL

(71) Applicant: HONDA MOTOR CO., LTD., Minato-ku, Tokyo (JP)

(72) Inventors: Takanori Maebashi, Wako (JP); Yoshiya Fujiwara, Wako (JP); Mitsumoto Kawai, Wako (JP); Nariaki Kuriyama, Wako (JP)

(73) Assignee: Honda Motor Co., Ltd., Tokyo (JP)

(*) Notice: Subject to any disclaimer, the term of this patent is extended or adjusted under 35 U.S.C. 154(b) by 7 days.

(21) Appl. No.: 15/245,745

(22) Filed: Aug. 24, 2016

(65) Prior Publication Data

US 2017/0059522 A1   Mar. 2, 2017

(30) Foreign Application Priority Data

Aug. 26, 2015   (JP) .................. 2015-166691

(51) Int. Cl.
| | |
|---|---|
| *H01J 37/20* | (2006.01) |
| *G01N 27/416* | (2006.01) |
| *H01M 14/00* | (2006.01) |
| *H01J 37/16* | (2006.01) |
| *H01M 10/42* | (2006.01) |
| *H01J 37/26* | (2006.01) |

(52) U.S. Cl.
CPC .......... *G01N 27/4168* (2013.01); *H01J 37/16* (2013.01); *H01J 37/20* (2013.01); *H01M 10/4285* (2013.01); *H01M 14/00* (2013.01); *H01J 37/26* (2013.01)

(58) Field of Classification Search
CPC .... H01J 37/20; H01J 2237/2003; H01J 37/26; H01J 2237/2007; H01J 2237/2002; H01J 2237/2008; H01J 2237/2602; H01J 2237/206; H01J 37/16
See application file for complete search history.

(56) References Cited

U.S. PATENT DOCUMENTS

| 8,872,129 | B2 * | 10/2014 | Damiano, Jr. .......... H01J 37/20 250/311 |
| 9,194,839 | B2 * | 11/2015 | Kuriyama ............ G01N 27/404 |
| 9,466,459 | B2 * | 10/2016 | Gardiner ................. H01J 37/20 |

(Continued)

FOREIGN PATENT DOCUMENTS

JP   2013-535795 A   9/2013

*Primary Examiner* — Wyatt Stoffa
(74) *Attorney, Agent, or Firm* — Carrier Blackman & Associates, P.C.; Joseph P. Carrier; William D. Blackman

(57) ABSTRACT

Substrates forming an overlapping portion of an analytical cell have through holes each having a shape tapered from an outer surface of the substrate facing to outside of the overlapping portion toward an inner surface thereof facing to inside thereof. An observation window is formed between the through holes facing each other. In the overlapping portion, at least one of negative and positive electrode active materials is provided between transmission membranes of the observation window, and at least one pillar is provided between first and second positions. At the first position, edge portions of the through holes of the outer surfaces are face-to-face with each other. At the second position, edge portions of the through holes of the inner surfaces are face-to-face with each other. At least one spacer is further provided at a position shifted from the first position toward a circumferential edge of the overlapping portion.

4 Claims, 18 Drawing Sheets

(56) References Cited

U.S. PATENT DOCUMENTS

| | | | | |
|---|---|---|---|---|
| 9,496,118 | B2* | 11/2016 | Kuriyama | H01J 37/20 |
| 2008/0135778 | A1* | 6/2008 | Liu | H01J 37/20 |
| | | | | 250/440.11 |
| 2008/0179518 | A1* | 7/2008 | Creemer | H01J 37/20 |
| | | | | 250/311 |
| 2010/0140497 | A1* | 6/2010 | Damiano, Jr. | B01L 3/508 |
| | | | | 250/440.11 |
| 2010/0143198 | A1* | 6/2010 | Damiano, Jr. | G01N 23/046 |
| | | | | 422/400 |
| 2010/0193398 | A1* | 8/2010 | Marsh | G02B 21/34 |
| | | | | 206/710 |
| 2011/0032611 | A1* | 2/2011 | Mick | H01J 37/20 |
| | | | | 359/395 |
| 2011/0079710 | A1* | 4/2011 | Damiano, Jr. | H01J 37/20 |
| | | | | 250/307 |
| 2012/0298883 | A1* | 11/2012 | Grogan | H01J 37/20 |
| | | | | 250/440.11 |
| 2013/0264476 | A1* | 10/2013 | Damiano, Jr. | H01J 37/20 |
| | | | | 250/307 |
| 2015/0293050 | A1* | 10/2015 | Kuriyama | G01N 27/404 |
| | | | | 250/453.11 |
| 2015/0294835 | A1* | 10/2015 | Kuriyama | H01J 37/20 |
| | | | | 250/440.11 |
| 2017/0003243 | A1* | 1/2017 | Maebashi | H01J 37/20 |

* cited by examiner

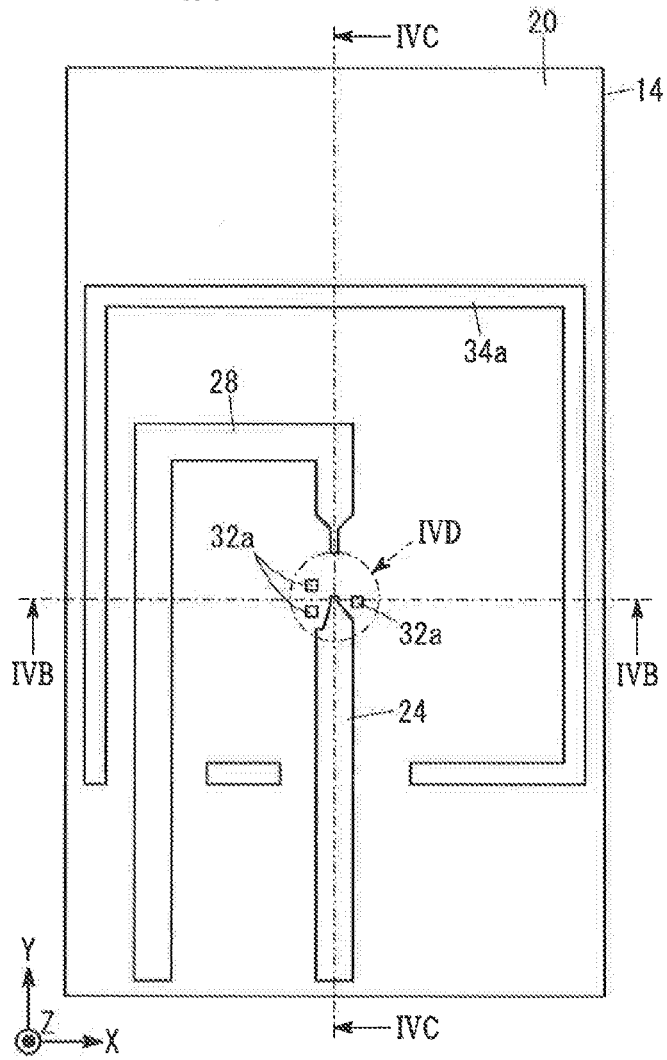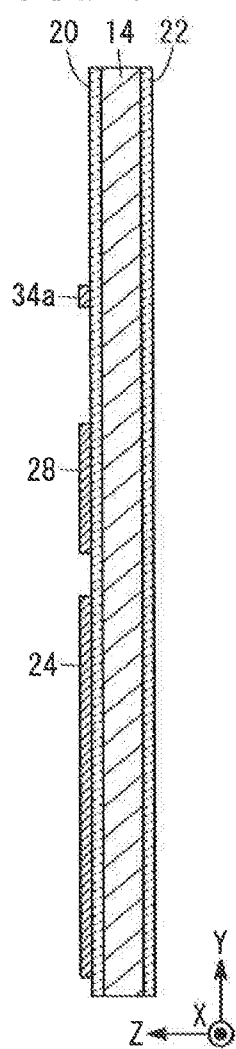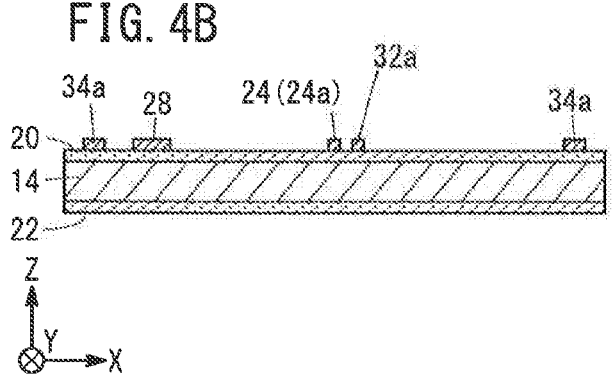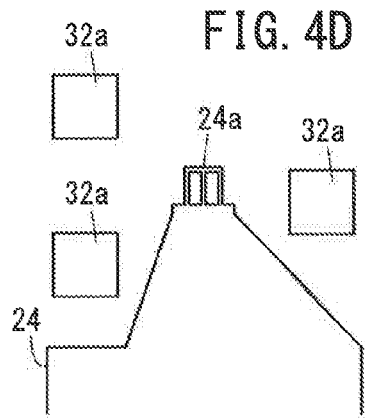

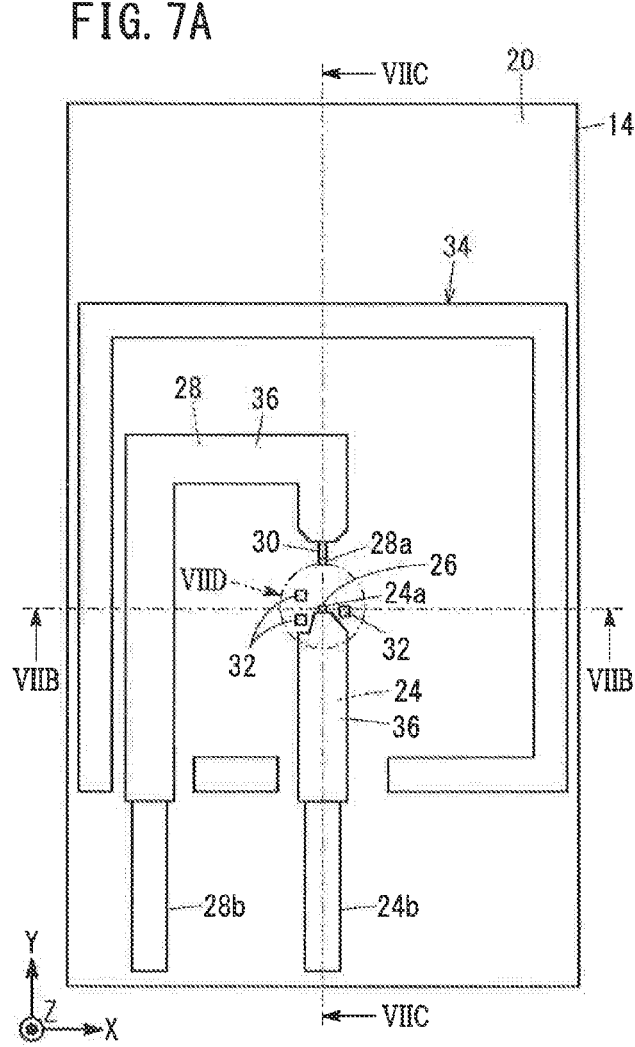
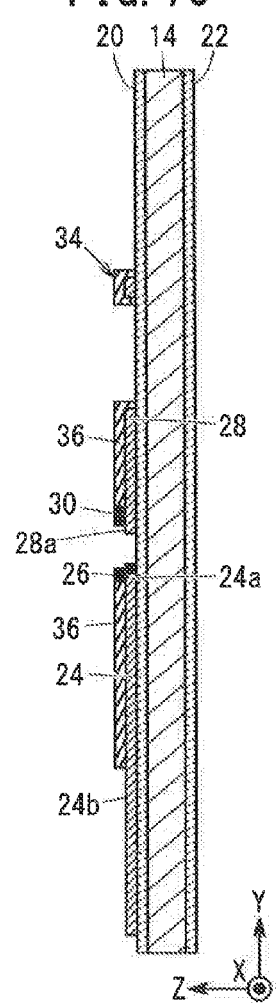
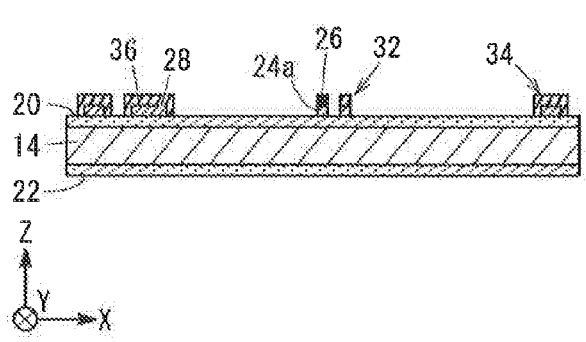
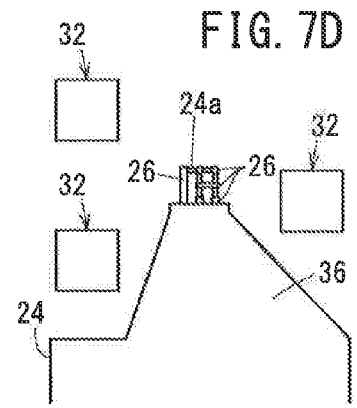
FIG. 7A
FIG. 7B
FIG. 7C
FIG. 7D

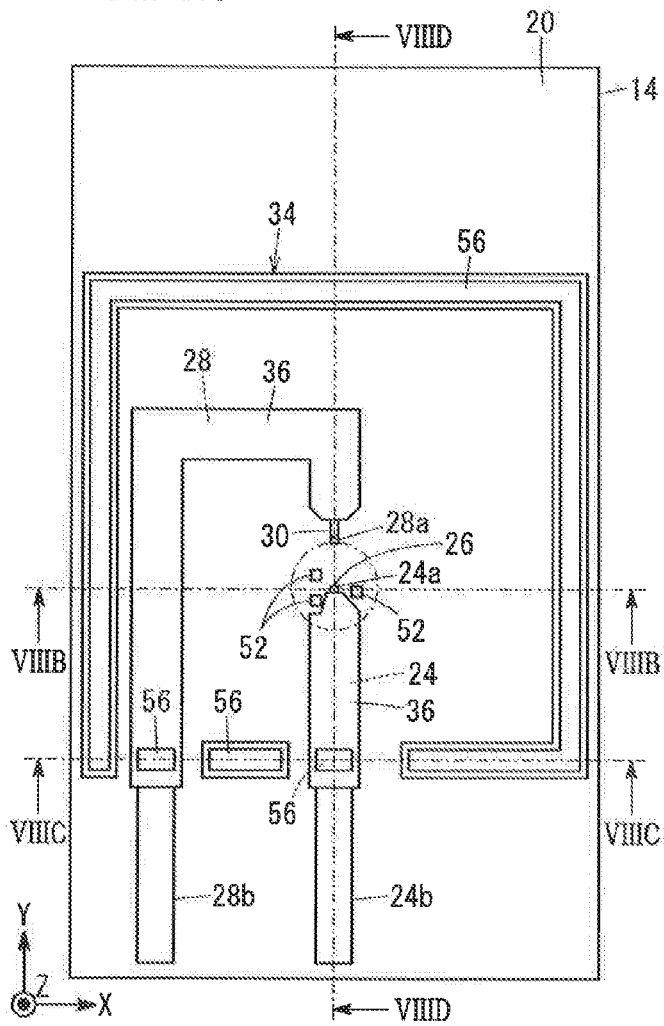
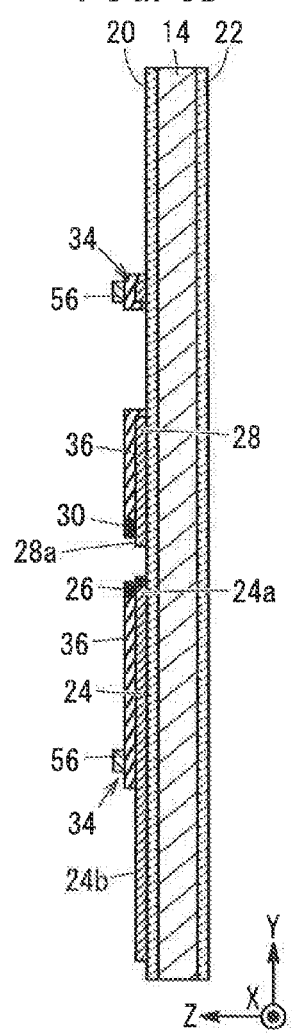
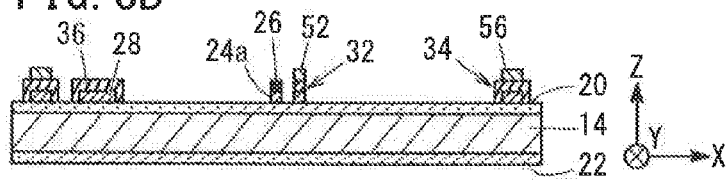
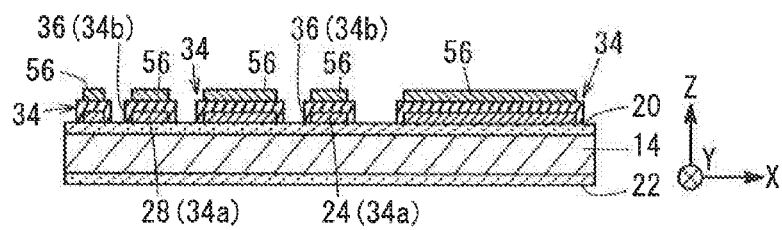

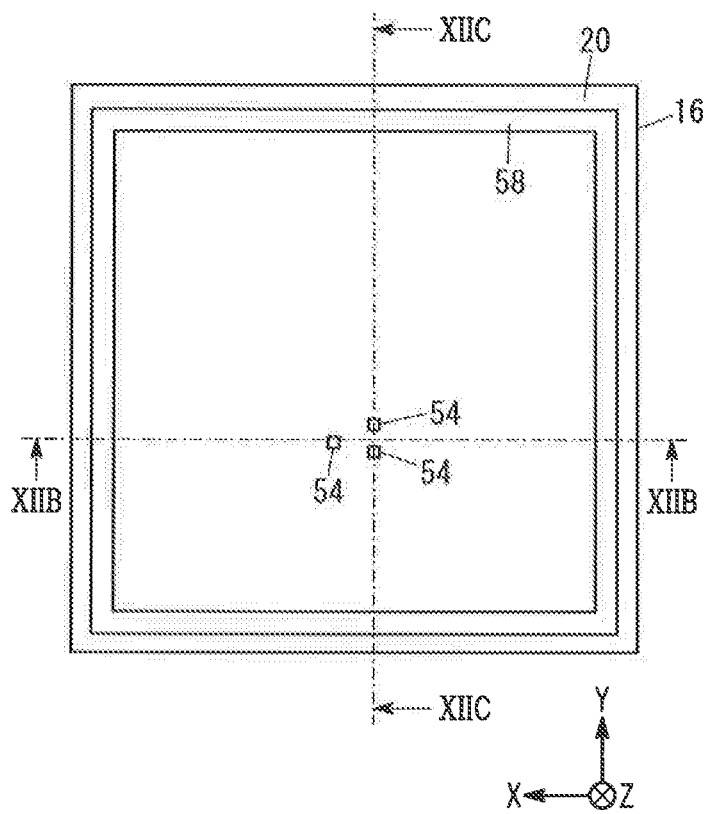
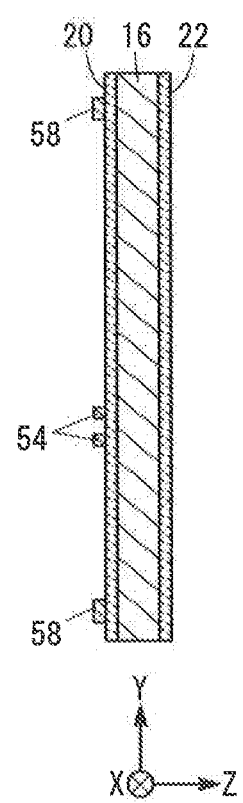
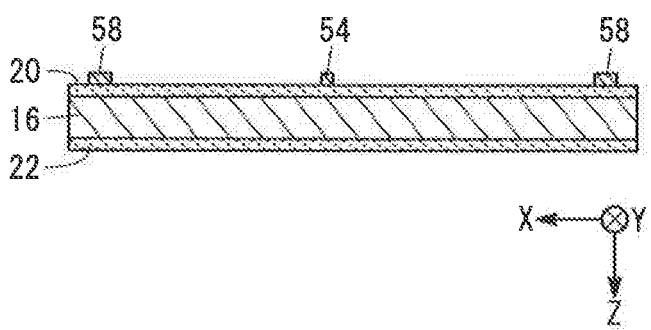

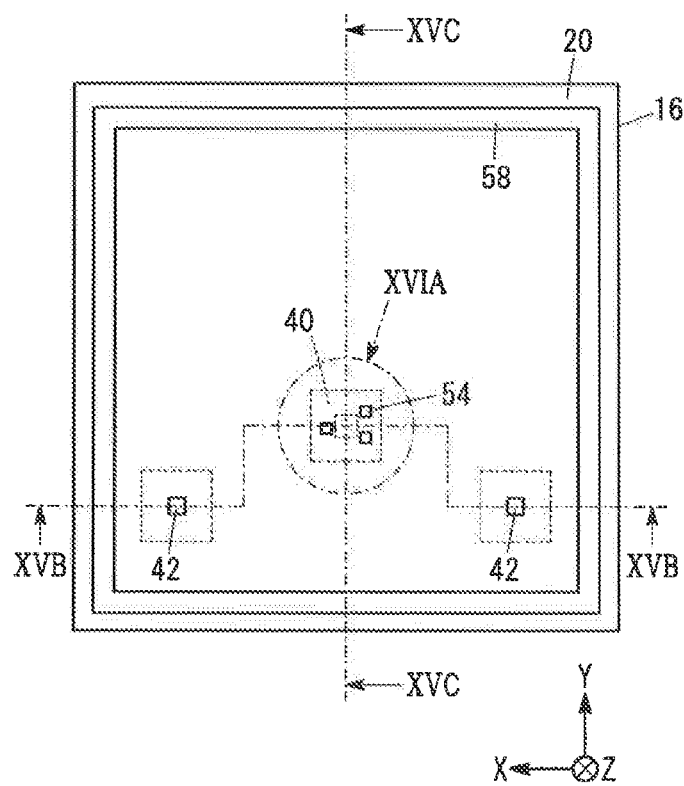
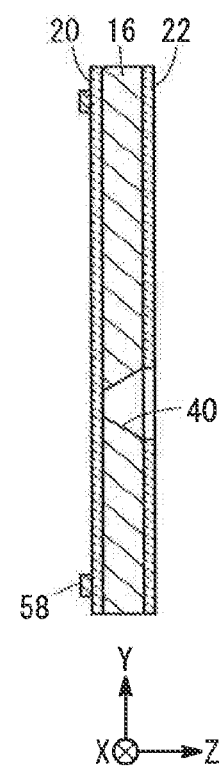
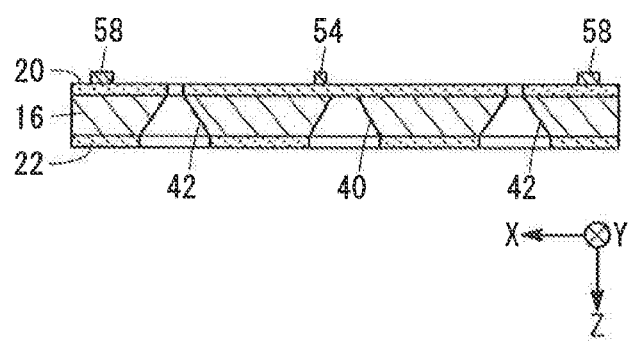

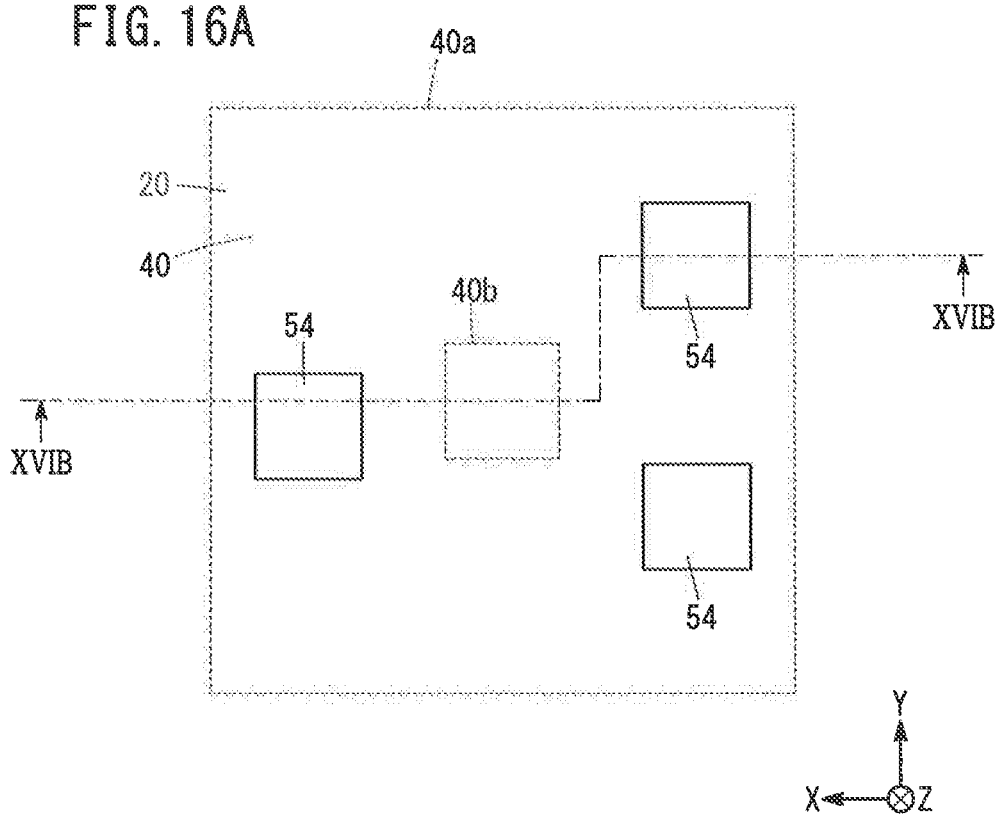
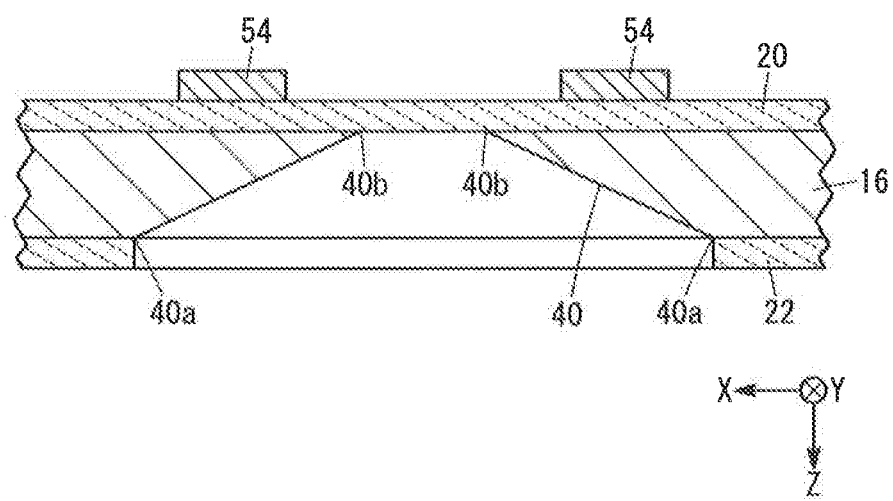

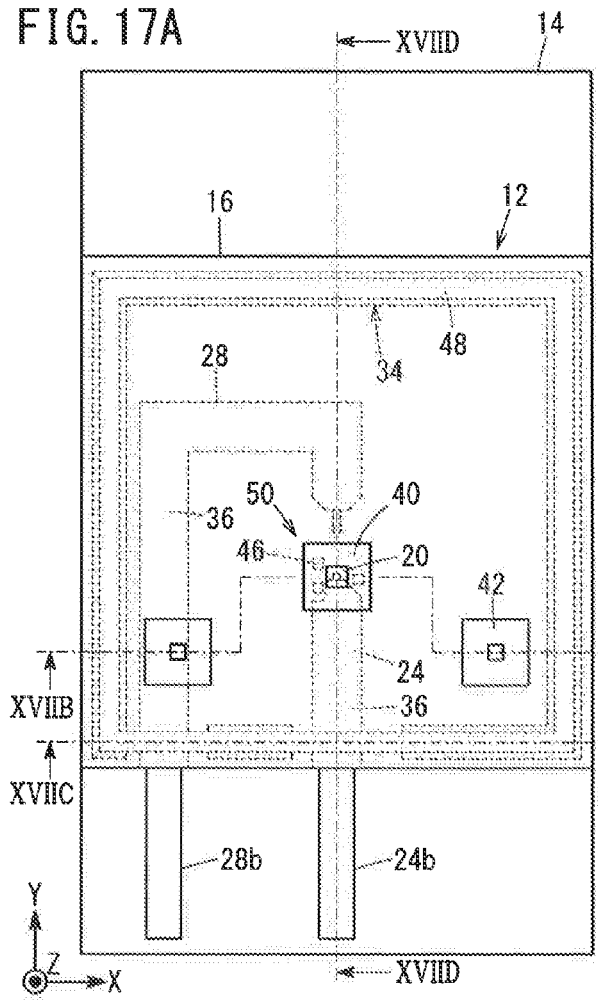
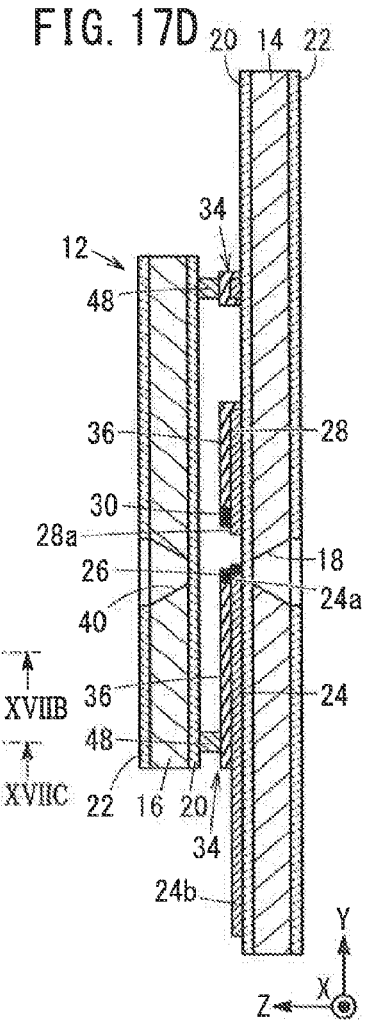
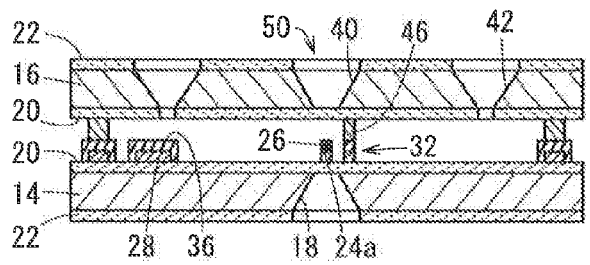
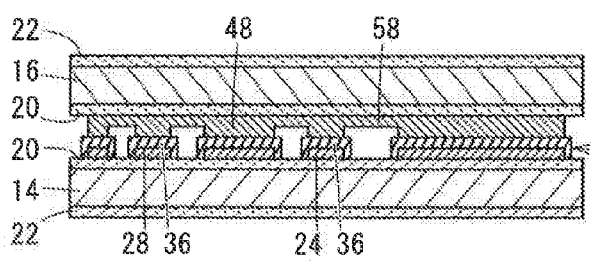

ANALYTICAL CELL

CROSS-REFERENCE TO RELATED APPLICATION

This application is based upon and claims the benefit of priority from Japanese Patent Application No. 2015-166691 filed on Aug. 26, 2015, the contents of which are incorporated herein by reference.

BACKGROUND OF THE INVENTION

Field of the Invention

The present invention relates to an analytical cell suitable for use, e.g., in an analysis of electrode reactions, etc. using an analytical instrument.

Description of the Related Art

As is well known, in an electric cell, a negative electrode active material and a positive electrode active material undergo electrode reactions, etc. in a charge-discharge process. In recent years, attempts have been made to analyze such electrode reactions during the charging/discharging process using an analytical instrument. For example, Japanese Laid-Open Patent Publication No. 2013-535795 (PCT) proposes an analytical cell which can be observed using a transmission electron microscope (TEM), and a holder for holding the analytical cell.

This analytical cell is formed by providing a negative electrode active material and a positive electrode active material (hereinafter also referred to as the electrode active material, collectively) in an overlapping portion formed by overlapping a pair of substrates. An observation window is formed at substantially the center of the overlapping portion in a direction along the surfaces of the substrates. An electron beam can be transmitted through the observation window in the overlapping direction of the overlapping portion, for allowing observation of electrode reactions, etc. in the electrode active materials. Specifically, a through hole is formed in each of the substrates. The through hole is covered with the transmission membrane from the inside of the overlapping portion. The electron beam can be transmitted through the transmission membrane. The observation window is formed between the through holes which face each other across the transmission membrane.

Further, in the analytical cell, a spacer is provided between the substrates, at an end of the overlapping portion remote from the observation window. In the structure, the substrates are spaced from each other by a predetermined distance. In the overlapping portion, at least one of the electrode active materials is provided between the transmission membranes of the observation window. Each of the electrode active materials is connected electrically to one end of the negative electrode collector or the positive electrode collector (hereinafter also referred to as the collector, collectively), in the overlapping portion. Since the other end of the collector is exposed to the outside of the overlapping portion, each of the electrode active materials is electrically connectable to the charging/discharging devices, etc. outside the overlapping portion through the collector.

That is, in the case of observing the analytical cell using a transmission electron microscope (TEM), firstly, the analytical cell is accommodated in a front end of a holder having a flow channel for allowing electrolytic solution to flow inside the overlapping portion. Thus, the electrolytic solution flows through the flow channel of the holder into the overlapping portion. The collectors are electrically connected to a charge-discharge tester or the like through the electric path of the holder. Consequently, it is possible to cause electrode reactions in the electrode active materials. At this time, an electron beam is transmitted through the observation window for carrying out the TEM observation. In this manner, it is possible to analyze the above electrode reactions.

SUMMARY OF THE INVENTION

In this regard, in the case of conducting a TEM observation of the analytical cell, when the electron beam is transmitted through the observation window, transmission of the electron beam tends to be obstructed by the electrolytic solution. Therefore, in order to obtain the observation result of the analytical cell highly accurately by improving the resolution of the image obtained as the observation result, it is required to reduce the distance by which the electron beam is transmitted through the electrolytic solution in the observation window. Stated otherwise, it is required to reduce the distance between the transmission membranes of the observation window.

On the other hand, if the distance between the transmission membranes of the observation window is excessively small, the constituent elements such as the electrode active materials are likely to be easily pressed and damaged between the transmission membranes. Consequently, the durability of the analytical cell is degraded. Therefore, for the purpose of improving the observation accuracy without degrading the durability of the analytical cell, it is desirable to adjust the distance between the transmission membranes of the observation window highly accurately in a manner that a small gap is formed between the constituent element and at least one of the transmission membranes.

However, in the above analytical cell, since only the distance between the substrates is adjusted by the thickness of the spacer provided at the end of the overlapping portion which is spaced from the observation window, it is difficult to adjust the distance between the transmission membranes of the observation window highly accurately.

Further, since the distance between the spacer and the observation window is large, for example, if an external force is applied to the analytical cell, the distance between the transmission membranes may be changed easily. That is, even if the distance between the transmission membranes of the observation window is adjusted, it is difficult to maintain the adjusted distance. Consequently, there is a concern that it is not possible to avoid the situation where the constituent elements are pressed and damaged between the transmission membranes.

A main object of the present invention is to provide an analytical cell in which it is possible to adjust the distance between transmission membranes of an observation window highly accurately, and suppress changes in the distance, whereby the observation accuracy is improved without degrading the durability.

According to an embodiment of the present invention, an analytical cell is provided. The analytical cell includes substrates overlapped with each other to form an overlapping portion. A negative electrode active material and a positive electrode active material are provided in the overlapping portion, and separately contact electrolytic solution. An observation window for transmission of an electron beam in an overlapping direction of the overlapping portion is provided in the overlapping portion. The substrates have respective through holes extending through the substrates in a thickness direction thereof. The substrates each have main surfaces on both sides thereof in the thickness direction.

Each of the through holes has a shape that is tapered from an outer surface of the main surfaces that faces to the outside of the overlapping portion, toward an inner surface of the main surfaces that faces to the inside of the overlapping portion. The through holes are covered with respective transmission membranes from the inner surface side, the transmission membranes each having an electron beam permeability. The observation window is formed between the through holes facing each other across the transmission membranes. At least one of the negative electrode active material and the positive electrode active material is formed between the transmission membranes of the observation window. In the overlapping portion, at least one pillar configured to maintain the distance between the transmission membranes of the observation window is provided between a first position and a second position. The first position is a position where edge portions of the through holes of the outer surfaces of the substrates are disposed face-to-face with each other in the overlapping direction. The second position is a position where edge portions of the through holes of the inner surfaces of the substrates are disposed face-to-face with each other in the overlapping direction. At least one spacer configured to maintain the distance between the substrates is provided at a position shifted from the first position toward a circumferential edge portion of the overlapping portion. A negative electrode collector and a positive electrode collector extend from the inside of the overlapping portion and protrude outside the overlapping portion, and are electrically connected respectively to the negative electrode active material and the positive electrode active material inside the overlapping portion.

In the overlapping portion of the analytical cell of the present invention, the distance between the substrates is maintained by the spacer, and the distance between the transmission membranes of the observation window is maintained by the pillar. Since this pillar is positioned between the first position and the second position in the overlapping portion, the pillar is positioned close to the observation window. In the structure, the distance between the substrates in the overlapping portion, in particular, the distance between the transmission membranes of the observation window can be adjusted highly accurately. Further, even in the case where an external force is applied to the analytical cell, changes in the distance between the transmission membranes can be suppressed effectively.

Therefore, in this analytical cell, the distance between the transmission membranes can be adjusted to be reduced to an extent that only a slight gap is formed between the constituent elements (e.g., at least one of the negative electrode active material and the positive electrode active material) disposed between the transmission membranes of the observation window and at least one of the transmission membranes, and the distance can be maintained. That is, in order to obtain a desired resolution in the TEM observation, etc., it is possible to reduce the distance between the transmission membranes of the observation window, and prevent the constituent elements from being pressed between the transmission membranes. As a result, it becomes possible to improve the observation accuracy without degrading the durability of the analytical cell.

In the analytical cell, preferably, the pillar includes at least three pillars that are not on the same straight line. In this case, changes in the distance between the transmission membranes of the observation window can be suppressed more effectively.

In the analytical cell, preferably, the pillar includes a pair of pillars that face each other across the observation window. In this case, changes in the distance between the transmission membranes of the observation window can be suppressed more effectively.

In the analytical cell, preferably, the pillar includes one pillar provided in the vicinity of a space between the negative electrode active material and the positive electrode active material that face each other, in the overlapping portion. In this case, owing to the pillar, the distance between the transmission membranes in the vicinity of the negative electrode active material and the positive electrode active material can be maintained suitably. Thus, it is possible to effectively suppress contact of the transmission membranes with the negative electrode active material and the positive electrode active material. Further, this pillar can ensure that a sufficient space is provided between the negative electrode active material and the positive electrode active material in the overlapping portion. Thus, even in the case where an external force is applied to the analytical cell, since each of the negative electrode active material and the positive electrode active material is placed in contact with the electrolytic solution, and the electrode reactions occur suitably, it is possible to improve the observation accuracy.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 4A is a plan view showing a state where a negative electrode collector, a positive electrode collector, a first base portion, and a first spacer layer are provided on the one surface of the first substrate in FIG. 3A;

FIG. 4B is a sectional end view taken along a line IVB-IVB indicated by arrows in FIG. 4A;

FIG. 4C is a sectional end view taken along a line IVC-IVC indicated by arrows in FIG. 4A;

FIG. 4D is an enlarged view showing an area around the first base portion indicated by an arrow IVD in FIG. 4A;

FIG. 7A is a plan view showing a state where a negative electrode active material is provided on the connector portion of the negative electrode collector in FIG. 6A;

FIG. 7B is a sectional end view taken along a line VIIB-VIIB indicated by arrows in FIG. 7A;

FIG. 7C is a sectional end view taken along a line VIIC-VIIC indicated by arrows in FIG. 7A;

FIG. 7D is an enlarged view showing an area around the negative electrode active material indicated by an arrow VIID in FIG. 7A;

FIG. 8A is a plan view showing a state where a first pillar precursor is formed on the second base portion in FIG. 7A, and a first spacer precursor is formed on the second spacer layer;

FIG. 8B is a sectional end view taken along a line VIIIB-VIIIB indicated by arrows in FIG. 8A;

FIG. 8C is a sectional end view taken along a line VIIIC-VIIIC indicated by arrows in FIG. 8A;

FIG. 8D is a sectional end view taken along a line VIIID-VIIID indicated by arrows in FIG. 8A;

FIG. 12A is a plan view showing a state where a second pillar precursor and a second spacer precursor are provided on one surface of the second substrate in FIG. 11A;

FIG. 12B is a sectional end view taken along a line XIIB-XIIB indicated by arrows in FIG. 12A;

FIG. 12C is a sectional end view taken along a line XIIC-XIIC indicated by arrows in FIG. 12A;

FIG. 15A is a plan view showing a state where the through hole and the injection holes are formed in the second substrate in FIG. 14A;

FIG. 15B is a sectional end view taken along a line XVB-XVB indicated by arrows in FIG. 15A;

FIG. 15C is a sectional end view taken along a line XVC-XVC indicated by arrows in FIG. 15A;

FIG. 16A is an enlarged view showing an area around the second pillar precursor indicated by an arrow XVIA in FIG. 15A;

FIG. 16B is a sectional end view taken along a line XVIB-XVIB indicated by arrows in FIG. 16A;

FIG. 17A is a plan view showing a state where the first substrate in FIG. 9A and the second substrate in FIG. 15A are overlapped with each other to form an overlapping portion;

FIG. 17B is a sectional end view taken along a line XVIIB-XVIIB indicated by arrows in FIG. 17A;

FIG. 17C is a sectional end view taken along a line XVIIC-XVIIC indicated by arrows in FIG. 17A;

FIG. 17D is a sectional end view taken along a line XVIID-XVIID indicated by arrows in FIG. 17A;

DESCRIPTION OF THE PREFERRED EMBODIMENTS

Figure 1A:
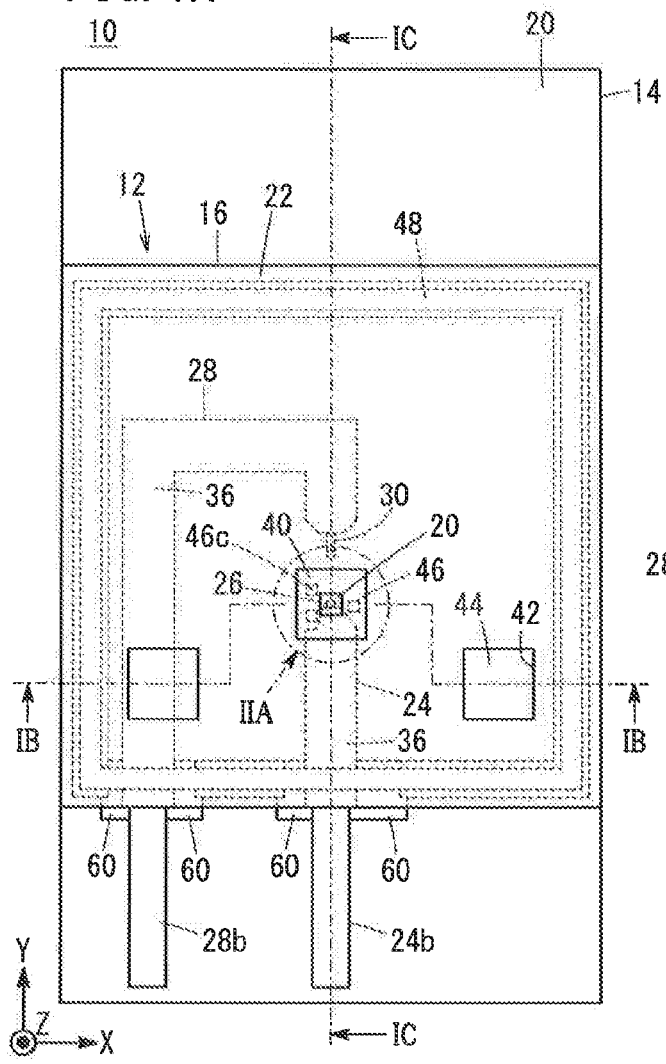
FIG. 1A is a plan view showing an analytical cell according to an embodiment of the present invention.

Hereinafter, preferred embodiments of an analytical cell according to the present invention will be described with reference to the accompanying drawings.

The analytical cell is suitable for use, e.g., in an analysis of electrode reactions, etc. in a negative electrode active material and a positive electrode active material based on electron beam transmission using various types of analytical instruments. For example, the analytical instrument may be a transmission electron microscope (TEM). In the case of using the TEM, the analytical cell is accommodated in a front end of a TEM holder, and an observation process is performed. Further, for example, the analytical cell may be any of a metal ion secondary cell of lithium, sodium, etc., a nickel-hydrogen cell, an alkaline-manganese cell, a metal ion air cell, a metal ion all solid cell, etc., and a fuel cell such as a solid polymer electrolyte fuel cell. Hereinafter, examples of an analytical cell made up of a lithium ion secondary cell will be described.

An analytical cell 10 according to an embodiment of the present invention will be described mainly with reference to FIGS. 1A to 1C, 2A and 2B. In the following description, for ease of understanding the invention, the X-axis, Y-axis, and Z-axis directions shown in the drawings are defined as the width, depth, and height (thickness) directions, respectively. In addition, in the X-axis, Y-axis, and Z-axis directions, the tip of the arrow will be referred to as one end, and the base end of the arrow will be referred to as the other end.

Figure 1C:
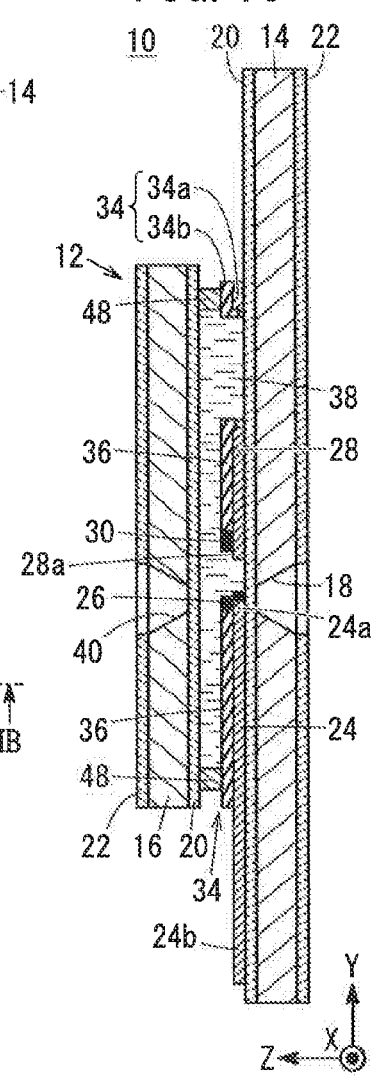
FIG. 1C is a sectional end view taken along a line IC-IC indicated by arrows in FIG. 1A.
Figure 1B:
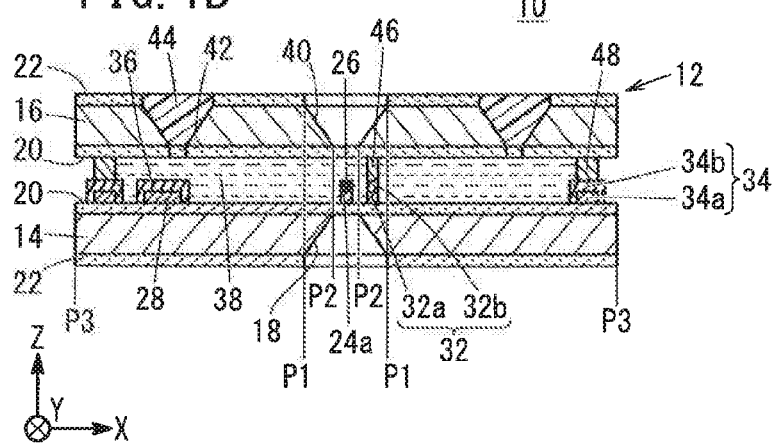
FIG. 1B is a sectional end view taken along a line IB-IB indicated by arrows in FIG. 1A.

The analytical cell 10 includes a first substrate 14 and a second substrate 16. The first substrate 14 and the second substrate 16 are overlapped with each other to form an overlapping portion 12. The first substrate 14 may be a substrate made of silicon (Si) with a silicon nitride ($Si_3N_4$) membrane formed thereon, a substrate made of Si with an oxide covering membrane of $SiO_2$, etc. formed thereon, or a substrate made of borosilicate glass, quartz ($SiO_2$), or the like. Further, as shown in FIG. 1C, a through hole 18 is formed in the first substrate 14, at a position slightly shifted from the center of the first substrate 14 in the depth direction toward the other end. The through hole 18 extends through the first substrate 14 in the thickness direction.

A transmission membrane 20 is provided on one surface of the first substrate 14 to cover the through hole 18, and a covering membrane 22 is provided on the other surface of the first substrate 14 in a manner to expose the through hole 18. The through hole 18 has a truncated square pyramid shape which is tapered from the other surface of the first substrate 14 with the covering membrane 22 formed thereon toward the one surface thereof with the transmission membrane 20 formed thereon.

Figure 2A:
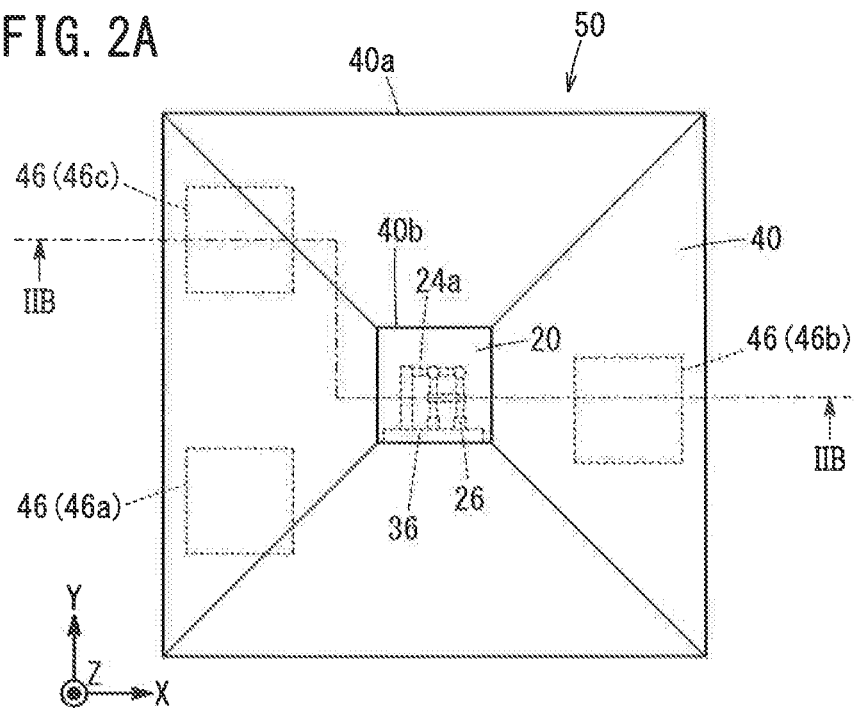
FIG. 2A is an enlarged view showing an area around an observation window indicated by an arrow IIA in FIG. 1A.
Figure 2B:
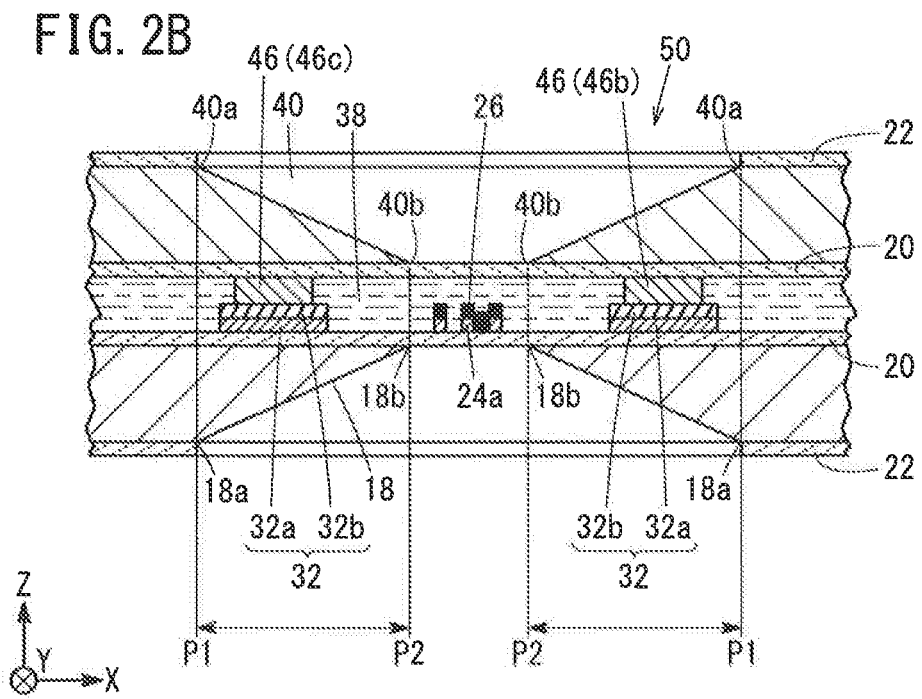
FIG. 2B is a sectional end view taken along a line IIB-IIB indicated by arrows in FIG. 2A.

That is, as shown in FIG. 2B in an enlarged manner, in the first substrate 14, an edge portion 18b of the through hole 18 of the one surface is positioned closer to the center of the through hole 18 in comparison with an edge portion 18a of the through hole 18 of the other surface.

The transmission membrane 20 is made of a material having an electron beam permeability (electron beam transparency) such as silicon nitride ($Si_3N_4$), silicon carbide (SiC), etc. The covering membrane 22 may be made of the same material as the transmission membrane 20.

A negative electrode collector 24, a negative electrode active material 26, a positive electrode collector 28, a positive electrode active material 30, pillar joint portions 32, and a spacer joint portion 34 are provided on the transmission membrane 20 of the first substrate 14. The material suitable for the negative electrode collector 24 includes tungsten (W), copper (Cu), stainless steel (SUS), carbon (C), etc. Further, in the negative electrode collector 24, a layered negative electrode active material 26 is disposed on a connector portion 24a positioned right above the through hole 18 through the transmission membrane 20 in contact with the connector portion 24a. The material suitable for forming the negative electrode active material 26 includes, for example, Li, Li alloy, $Li_4Ti_5O_{12}$, Si, Ge, Sn, Sn alloy, Al, Al alloy, Si oxide, Sn oxide, Al oxide, carbon (C), etc.

Figure 5A:
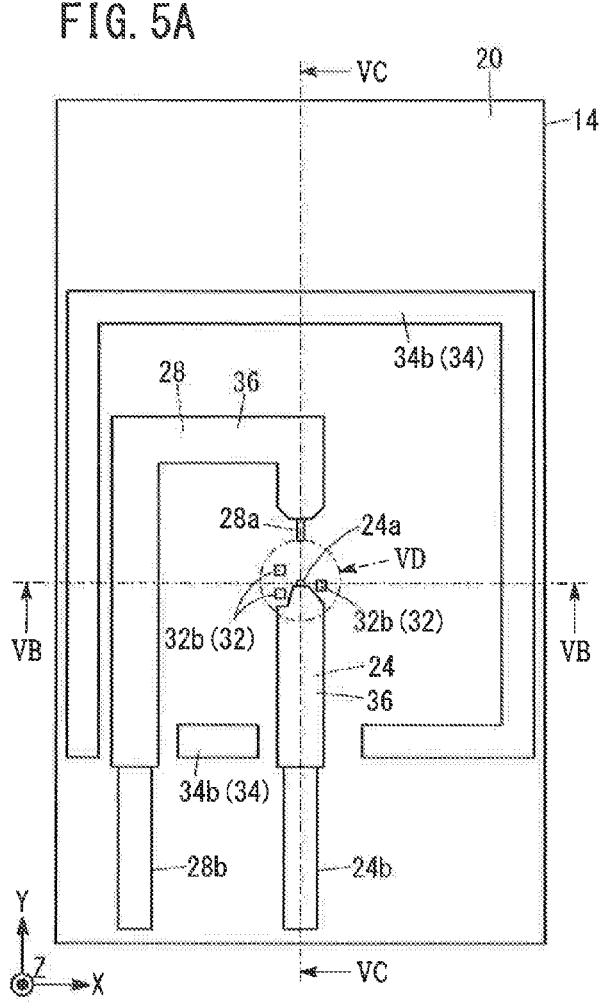
FIG. 5A is a plan view showing a state where an insulating membrane is provided on portions of the negative electrode collector and the positive electrode collector in FIG. 4A except exposed portions and connector portions, a second base portion is provided on the first base portion, and a second spacer layer is provided on the first spacer layer.
Figure 5C:
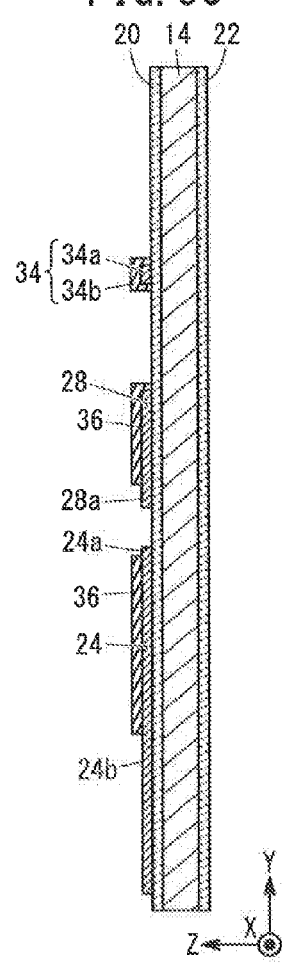
FIG. 5C is a sectional end view taken along a line VC-VC indicated by arrows in FIG. 5A.
Figure 5B:
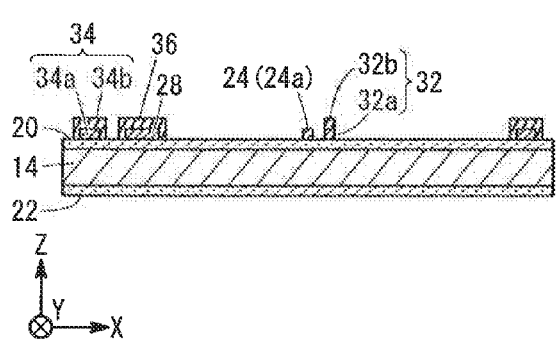
FIG. 5B is a sectional end view taken along a line VB-VB indicated by arrows in FIG. 5A.
Figure 5D:
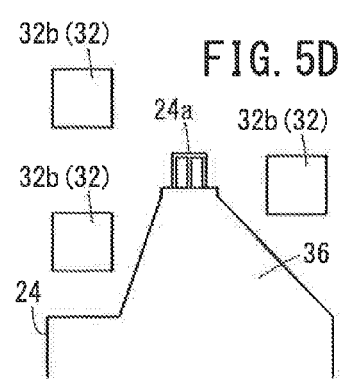
FIG. 5D is an enlarged view showing an area around the second base portion indicated by an arrow VD in FIG. 5A.

Further, the connector portion 24a and the negative electrode active material 26 may have a shape and a layout configuration shown in FIGS. 5D and 7D. That is, as shown in FIG. 7D, the negative electrode active material 26 may comprise six separate pieces including three types of quadrangular shape and one type of circular shape, and these pieces may be provided on the connector portion 24a, or may extend across the connector portion 24a and the transmission membrane 20. In this case, it becomes easier to observe the behavior of deformation of the negative electrode active material 26, etc. resulting from electrode reactions.

The material suitable for the positive electrode collector 28 includes gold (Au), platinum (Pt), carbon (C), aluminum (Al), etc. Further, on the transmission membrane 20, the layered positive electrode active material 30 is disposed on a connector portion 28a of the positive electrode collector 28 facing the connector portion 24a of the negative electrode collector 24 in contact with the connector portion 28a. The positive electrode active material 30 may include, for example, $LiCoO_2$, $LiMnO_2$, $LiMn_2O_4$, $LiNiO_2$, $LiFePO_4$, $Li_2FePO_4F$, $LiCo_{1/3}Ni_{1/3}Mn_{1/3}O_2$, or Li ($Li_aNi_xMn_yCo_z$) $O_2$, etc.

The negative electrode collector 24 and the positive electrode collector 28 including end walls thereof, but excluding the connector portions 24a, 28a and exposed portions 24b, 28b, which protrude outside the overlapping portion 12 as described later, are covered with electrically insulating membranes 36. In this structure, in the overlapping portion 12, the insulating membranes 36 avoid contact of the negative electrode collector 24 and the positive electrode collector 28 with electrolytic solution 38 contained in the overlapping portion 12. Therefore, it is possible to suppress occurrence of side reactions, which are different from the electrode reactions in the negative electrode active material 26 and the positive electrode active material 30, in the negative electrode collector 24 and the positive electrode collector 28. Consequently, it becomes possible to analyze the electrode reactions as the analysis subjects highly accurately.

The pillar joint portion 32 is formed by stacking a first base portion 32a on the transmission membrane 20, and stacking a second base portion 32b on the first base portion 32a. Further, the spacer joint portion 34 is formed by stacking a first spacer layer 34a on the transmission membrane 20, and stacking a second spacer layer 34b on the first spacer layer 34a. End walls of the first spacer layer 34a are covered with the second spacer layer 34b. For example, each of the first base portion 32a and the first spacer layer 34a may be made of the same material as the negative electrode collector 24 and the positive electrode collector 28. Further, each of the second base portion 32b and the second spacer layer 34b may be made of the same material as the above insulating membrane 36. That is, as shown in FIG. 8C, the negative electrode collector 24 and the positive electrode collector 28 partially have the function as the first spacer layer 34a, and the insulating membrane 36 partially has the function of the second spacer layer 34b.

The second substrate 16 is made of the same material as the first substrate 14. The width and the height of the second substrate 16 are substantially the same as the width and the height of the first substrate 14, and the depth of the second substrate 16 is smaller than the depth of the first substrate 14. A through hole 40 is formed in the second substrate 16 at a position slightly shifted from the center in the depth direction toward the other end. The through hole 40 extends through the second substrate 16 in the thickness direction. The through hole 40 has a truncated square pyramid shape as in the case of the through hole 18 of the first substrate 14. That is, as shown in FIGS. 2A and 2B in an enlarged manner, also in the second substrate 16, in comparison with an edge portion 40a of the through hole 40 of the other surface, an edge portion 40b of the through hole 40 of one surface is positioned closer to the center of the through hole 40.

Further, two injection ports 42 are formed in the second substrate 16 at positions closer to the other end in the depth direction than the through hole 40. The injection ports 42 extend through the second substrate 16 in the thickness direction. A transmission membrane 20 is provided on one surface of the second substrate 16 in a manner to cover the through hole 40, and expose the injection ports 42. A covering membrane 22 is provided on the other surface of the second substrate 16 in a manner to expose the through hole 40 and the injection ports 42.

As described later, the injection ports 42 are formed for injecting the electrolytic solution 38 into the overlapping portion 12. After injection of the electrolytic solution 38, the injection ports 42 are closed by seal members 44 of epoxy resin, etc.

The first substrate 14 and the second substrate 16 (hereinafter also referred to as the "substrate" collectively) having the above constituent elements are overlapped with each other such that the one surface of the first substrate 14 and the one surface of the second substrate 16 face each other to form the overlapping portion 12. That is, among main surfaces of each of the substrates 14, 16 on both sides in the thickness direction, the other surface where the covering membrane 22 is provided is an outer surface oriented to the outside of the overlapping portion 12, and the one surface where the transmission membrane 20 is provided is an inner surface oriented to the inside of the overlapping portion 12.

Pillars 46 and a spacer 48 formed as described later are interposed between the substrates 14, 16 in the overlapping portion 12. In the structure, the substrates 14, 16 are positioned such that the through holes 18, 40 face each other across the transmission membranes 20. In the state where the distance between the substrates 14, 16 is maintained at a predetermined distance in correspondence with the heights of the pillars 46 and the spacer 48, etc., the substrates 14, 16 are joined together. That is, in the overlapping portion 12, an observation window 50 for allowing transmission of an electron beam through the transmission membranes 20 is formed between the through holes 18, 40, and a negative electrode active material 26 is provided between the transmission membranes 20 of the observation window 50.

Further, as described above, since the depth of the second substrate 16 is small in comparison with the depth of the first substrate 14, both ends of the first substrate 14 in the depth direction protrude out from the overlapping portion 12. The portions of the negative electrode collector 24 and the positive electrode collector 28 on the first substrate 14 that protrude out from this overlapping portion 12 form exposed portions 24b, 28b. That is, the negative electrode collector 24 and the positive electrode collector 28 are provided on the transmission membrane 20 of the first substrate 14 such that the negative electrode collector 24 and the positive electrode collector 28 extend from the inside of the overlapping portion 12 and the exposed portions 24b, 28b are exposed from the overlapping portion 12.

In this regard, as shown in FIG. 2B in an enlarged manner, in the overlapping portion 12, a position where the edge portions 18a, 40a of the through holes 18, 40 of the outer surfaces of the substrates 14, 16 are disposed face-to-face with each other in the overlapping direction (height direction) of the overlapping portion 12 is referred to as a first position P1. Further, in the overlapping portion 12, a position where the edge portions 18b, 40b of the through holes 18, 40 of the inner surfaces of the substrates 14, 16 are disposed face-to-face with each other in the overlapping direction is referred to as a second position P2. In this case, as described above, since the through holes 18, 40 are tapered from the outer-surface side toward the inner-surface side of the substrates 14, 16, the second position P2 is closer to the center of the observation window 50 in comparison with the first position P1. In the overlapping portion 12, pillars 46 are provided between the first position P1 and the second position P2 (an area shown by arrows in FIG. 2B). In the structure, owing to the pillars 46, the distance between the transmission membranes 20 of the observation window 50 is maintained.

It is sufficient that at least one pillar 46 is provided between the first position P1 and the second position P2. However, preferably, three pillars 46a, 46b, 46c are arranged as shown in FIG. 2A. These pillars 46a, 46b, and 46c contact the substrate 16 at three points which are not on the same straight line. Stated otherwise, the pillars 46a, 46b, and 46c contact the substrate 16 at three points which forms a plane. Among these pillars 46a, 46b, and 46c, the pillars 46a and 46b face each other across the observation window 50, and the pillar 46c and the pillar 46b face each other across the observation window 50. Further, as shown in FIG. 1A, the pillar 46c is provided adjacent to an area between the negative electrode active material 26 and the positive electrode active material 30 which face each other.

As described above, by arranging the pillars 46a to 46c (hereinafter also referred to as the "pillar 46", collectively), without obstructing contact of the negative electrode active material 26 and the positive electrode active material 30 with the electrolytic solution 38, it is possible to suppress variation in the distance between the transmission membranes 20 of the observation window 50. In the illustrated embodiment of the present invention, the contact surface of the pillar 46 which contacts the substrate 16 has a quadrangular shape. However, the present invention is not limited in this respect. The contact surface may have another polygonal shape, or a circular shape. Further, preferably, the maximum length of the contact surface of the pillar 46 is, e.g., in a range of 40 µm to 300 µm. Further, preferably, the distance between the pillar 46 and the second position P2 is in a range of 50 µm to 500 µm.

As described later, the pillar 46 is formed by solid state bonding of a first pillar precursor 52 (see FIGS. 10A and 10B, etc.) formed on the pillar joint portion 32 of the first substrate 14 and a second pillar precursor 54 (see FIGS. 16A and 16B, etc.) formed on the transmission membrane 20 of the second substrate 16. It should be noted that the term "solid state bonding (welding)" used in this specification means "General term for the method of welding performed at a temperature less than or equal to the melting point of base material. In the method, welding of solid state materials are performed in a pressurized state or a non-pressurized state without using brazing material." defined in JISZ3001-2 "Welding Vocabulary Part 2: Welding Processes 4.2.7. Solid State Bonding No. 22701".

The material suitable for the first pillar precursor 52 and the second pillar precursor 54 includes a metal such as gold (Au), copper (Cu), or aluminum (Al), or an inorganic material such as $SiO_2$, Si. The materials of the first pillar precursor 52 and the second pillar precursor 54 may be the same, or may be different from each other. In the case where the first pillar precursor 52 and the second pillar precursor 54 are made of metal, as the solid state bonding, any of various methods, including hot pressure welding, cold pressure welding, diffusion welding, and friction pressure welding may be adopted. Further, in the case where the first pillar precursor 52 and the second pillar precursor 54 are made of inorganic material, for example, a bonding method by bringing the bonding surfaces activated by surface treatment into contact with each other may be adopted. In such a method, it is not essential to apply any load for the bonding process.

In the overlapping portion 12, the spacer 48 is provided at a position shifted from the first position P1 toward the circumferential edge portion P3 (see FIG. 1B) of the overlapping portion 12, and maintains the distance between the substrates 14, 16. In the embodiment of the present invention, as shown in FIG. 1A, the spacer 48 seals sides of the overlapping portion 12 except a side thereof extending in the width direction at the other end in the depth direction (hereinafter referred to as the wiring line side), i.e., seals three sides of the overlapping portion 12. The spacer 48 is formed continuously along the three sides, inward of the overlapping portion 12 Further, in the wiring line side, the spacer 48 is not formed adjacent to a transverse section extending across the wiring line side, in order for the negative electrode collector 24 and the positive electrode collector 28 to protrude from the inside to the outside of the overlapping portion 12. Stated otherwise, the spacer 48 is formed in an area of the wiring line side other than a portion adjacent to the transverse section. That is, the spacer 48 is formed on the transverse section as well (see FIG. 18A and FIG. 18B).

Figure 9A:
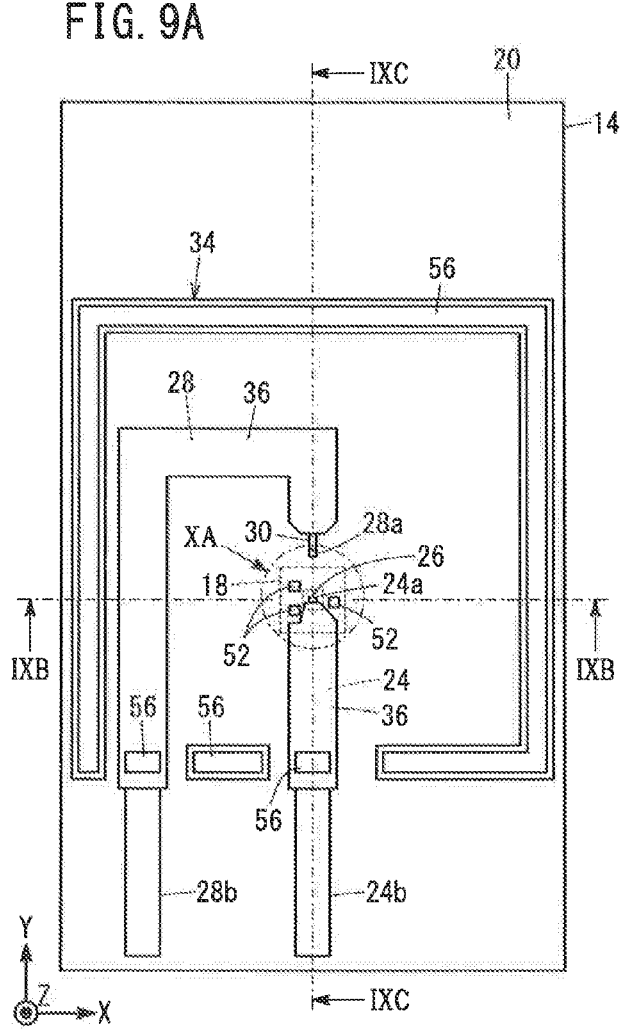
FIG. 9A is a plan view showing a state where a through hole is formed in the first substrate in FIG. 8A.
Figure 9C:
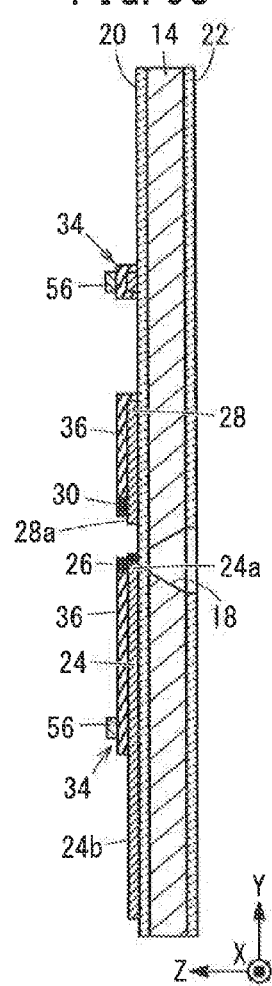
FIG. 9C is a sectional end view taken along a line IXC-IXC indicated by arrows in FIG. 9A.
Figure 9B:
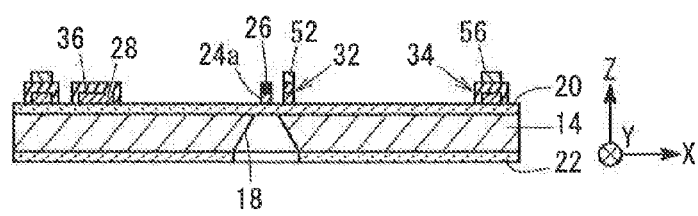
FIG. 9B is a sectional end view taken along a line IXB-IXB indicated by arrows in FIG. 9A.

As described later, this spacer 48 is formed by solid state bonding of a first spacer precursor 56 (see FIGS. 9A to 9C, etc.) formed on the spacer joint portion 34 of the first substrate 14 and a second spacer precursor 58 (see FIGS. 15A to 15C, etc.) formed on the transmission membrane 20 of the second substrate 16. The first spacer precursor 56 and the second spacer precursor 58 are made of the same material as the first pillar precursor 52 and the second pillar precursor 54 suitably. In the same manner as the pillar 46, the first spacer precursor 56 and the second spacer precursor 58 are joined by solid state bonding to form the spacer 48.

In the wiring line side of the overlapping portion 12, for example, a seal member 60 of epoxy resin, etc. is provided in the area which is not sealed by the spacer 48 (area adjacent to the transverse section). In this structure, a liquid tight space is formed in the overlapping portion 12, and filled with the electrolytic solution 38. Therefore, in the analytical cell 10, it is not required to generate flow of the electrolytic solution 38 in the overlapping portion 12. Therefore, it is possible to reduce the pressure of the electrolytic solution 38 applied to the substrates 14, 16. Accordingly, it is possible to reduce the distance between the substrates 14, 16, and reduce the overall size of the analytical cell 10.

As the electrolytic solution 38, for example, it is possible to suitably use solution obtained by adding supporting electrolyte such as lithium hexafluorophosphate ($LiPF_6$) of about 1M to propylene carbonate (PC), ethylene carbonate (EC), dimethyl carbonate (DMC), diethyl carbonate (DEC), ethyl methyl carbonate (EMC), vinylene carbonate (VC), etc.

The analytical cell 10 basically has the structure as described above. In the overlapping portion 12, the negative electrode active material 26 and the positive electrode active material 30 on the connector portions 24a, 28a of the negative electrode collector 24 and the positive electrode collector 28, separately contact the electrolytic solution 38. The negative electrode collector 24 and the positive electrode collector 28 extend from the connector portions 24a, 28a across the wiring line sides, and the exposed portions 24b, 28b are exposed to the outside of the overlapping portion 12. That is, the negative electrode active material 26 and the positive electrode active material 30 can be electrically connected to the outside of the overlapping portion 12 through the negative electrode collector 24 and the positive electrode collector 28.

For example, in the TEM observation of the analytical cell 10, firstly, the analytical cell 10 is placed on the TEM holder (not shown) in such a manner that the observation window 50 faces an electron beam irradiation part of the TEM. Then, the exposed portions 24b, 28b are electrically connected to the charge-discharge tester or the like, through an electrical path (not shown) provided in the holder to cause the electrode reactions as the observation subjects in the negative electrode active material 26 and the positive electrode active material 30.

The analytical cell 10 may be produced by a known semiconductor process (see, e.g., International Publication No. WO 2008/141147). Hereinafter, a method of producing the analytical cell 10 according to the embodiment of the present invention will be described below with reference to FIGS. 3A to 18B. It is a matter of course that the method of producing the analytical cell 10, and the order of steps or processes for production of the analytical cell 10 are not limited to those described in the following description. In this example, the first substrate 14, the second substrate 16, and the negative electrode active material 26 are made of silicon (Si), the positive electrode active material 30 is made of lithium cobaltate ($LiCoO_2$), the transmission membrane 20, the covering membrane 22, and the insulating membrane 36 are made of silicon nitride ($Si_3N_4$), and the negative electrode collector 24 and the positive electrode collector 28 are made of tungsten (W).

The analytical cell 10 can be obtained by forming the above constituent elements on the first substrate 14 and the second substrate 16 separately, and then bonding the first pillar precursor 52 and the second pillar precursor 54 together, and the first spacer precursor 56 and the second spacer precursor 58 together by solid state bonding. Then, at the outset, steps of providing the constituent elements including the first pillar precursor 52 and the first spacer precursor 56 on the first substrate 14 will be described.

Figure 3A:
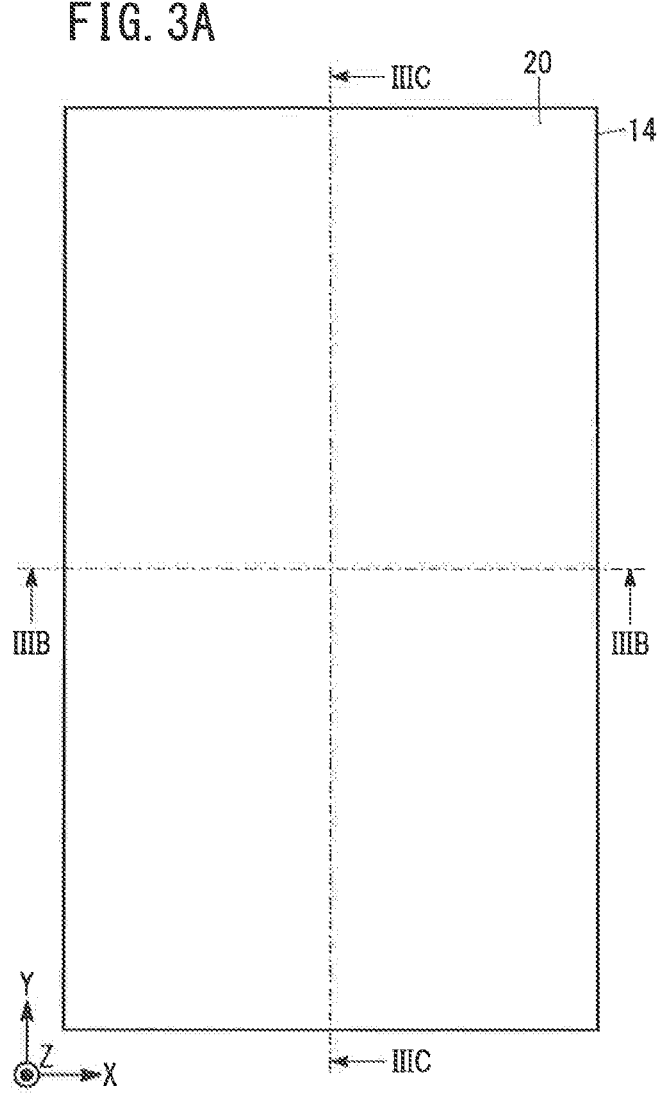
FIG. 3A is a plan view showing a transmission membrane of a first substrate having the transmission membrane on one surface and a covering membrane on the other surface.
Figure 3C:
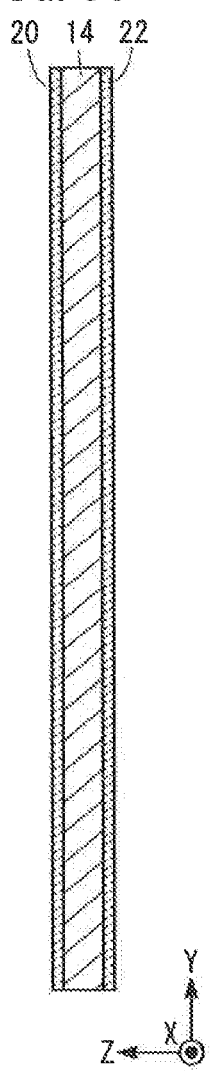
FIG. 3C is a cross sectional view taken along a line IIIC-IIIC indicated by arrows in FIG. 3A.
Figure 3B:
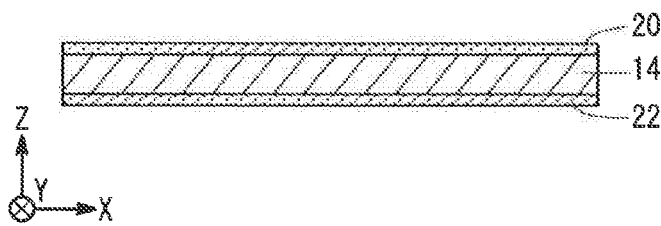
FIG. 3B is a cross sectional view taken along a line IIIB-IIIB indicated by arrows in FIG. 3A.

Firstly, as shown in FIGS. 3A to 3C, both surfaces of the first substrate 14 are polished, and each of the surfaces of the first substrate 14 is covered with a silicon nitride membrane by chemical vapor deposition (CVD). The silicon nitride membrane formed on the one surface of the first substrate 14 is used as the transmission membrane 20, and the silicon nitride membrane formed on the other surface of the first substrate 14 is used as the covering membrane 22.

Next, the transmission membrane 20 of the first substrate 14 is covered with a photoresist (not shown), and a photolithography process is performed. In the photolithography process, the photoresist is removed only on portions of the transmission membrane 20 where the negative electrode collector 24, the positive electrode collector 28, the pillar joint portion 32, and the spacer joint portion 34 should be formed, whereby only the portions of the transmission membrane 20 are exposed to outside.

Next, using the physical vapor deposition (PVD) method, one surface of the first substrate 14 is covered with a tungsten membrane, and thereafter, the entire photoresist is removed (by lift-off processing). As a result, as shown in FIGS. 4A to 4C, the negative electrode collector 24, the positive electrode collector 28, the first base portions 32a of the pillar joint portions 32, and the first spacer layer 34a of the spacer joint portion 34, which are made up of the tungsten membranes, are formed on the transmission membrane 20 of the first substrate 14. In this case, the number and layout of the first base portions 32a, and the shape of the connector portion 24a of the negative electrode collector 24 are set as shown in FIG. 4D.

Next, the one surface of the first substrate 14 is covered with a silicon nitride membrane by chemical vapor deposition (CVD). Then, this silicon nitride membrane is covered with a photoresist, and a photolithography process is performed. As a result of this process, the photoresist is left only on portions of the silicon nitride membrane that cover a portion of the negative electrode collector 24 excluding the connector portion 24a and the exposed portion 24b, and a portion of the positive electrode collector 28 excluding the connector portion 28a and the exposed portion 28b, and also cover the first base portions 32a and the first spacer layer 34a. It should be noted that the photoresist is also left on portions of the silicon nitride membrane that cover the end walls of the above portions of the negative electrode collector 24 and the positive electrode collector 28, and the end walls of the first spacer layer 34a.

Next, for example, a dry etching process such as a reactive ion etching process is carried out using the photoresist as a mask. In this process, the silicon nitride membrane covered with the residual photoresist as described above are protected. Thereafter, the entire photoresist is removed. Consequently, as shown in FIGS. 5A to 5D, the silicon nitride membrane is formed so as to cover the portion of the negative electrode collector 24 excluding the connector portion 24a and the exposed portion 24b, the portion of the positive electrode collector 28 excluding the connector portion 28a and the exposed portion 28b, the first base portion 32a, and the first spacer layer 34a. It is a matter of course that the end walls of the above portions of the negative electrode collector 24 and the positive electrode collector 28, and the end walls of the first spacer layer 34a are also covered with the silicon nitride membrane.

The part of the silicon nitride membrane covering the negative electrode collector 24 and the positive electrode collector 28 form the insulating membrane 36, and the part of the silicon nitride membrane covering the first base portions 32a forms second base portions 32b, and the silicon nitride membrane covering the first spacer layer 34a forms the second spacer layer 34b. That is, the first base portions 32a and the second base portions 32b form the pillar joint portions 32, and the first spacer layer 34a and the second spacer layer 34b form the spacer joint portion 34.

Next, the one surface of the first substrate 14 is covered with a photoresist, and a photolithography process is performed. In the photolithography process, the photoresist on a portion of the one surface where the positive electrode active material 30 should be formed is removed. As a result, only the portion of the connector portion 28a of the positive electrode collector 28 where the positive electrode active material 30 should be formed is exposed.

Figure 6A:
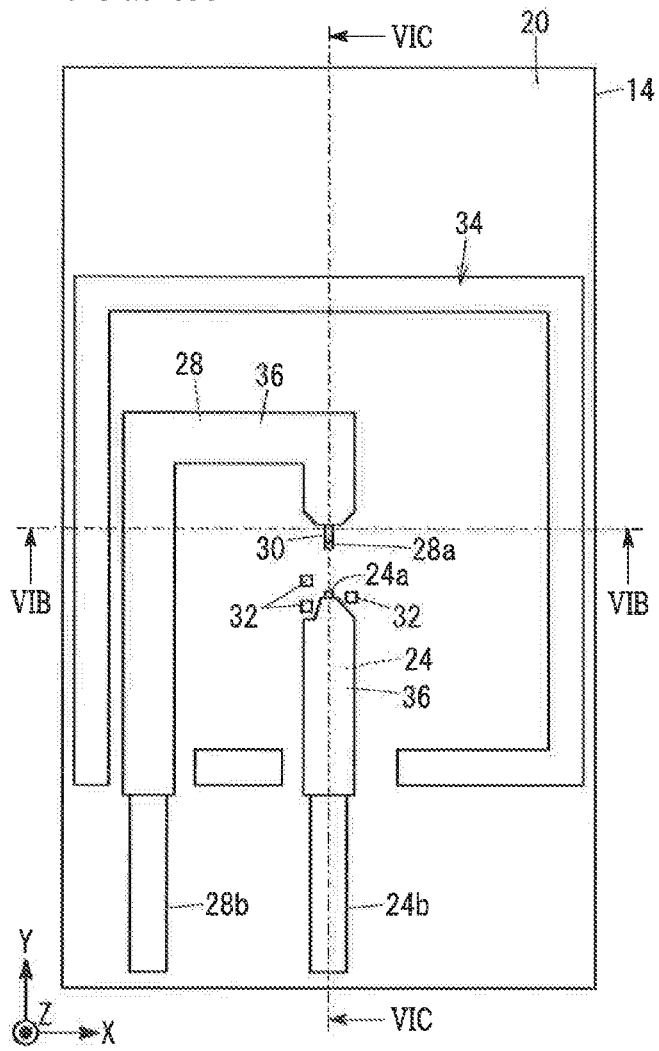
FIG. 6A is a plan view showing a state where a positive electrode active material is provided on the connector portion of the positive electrode collector in FIG. 5A.
Figure 6C:
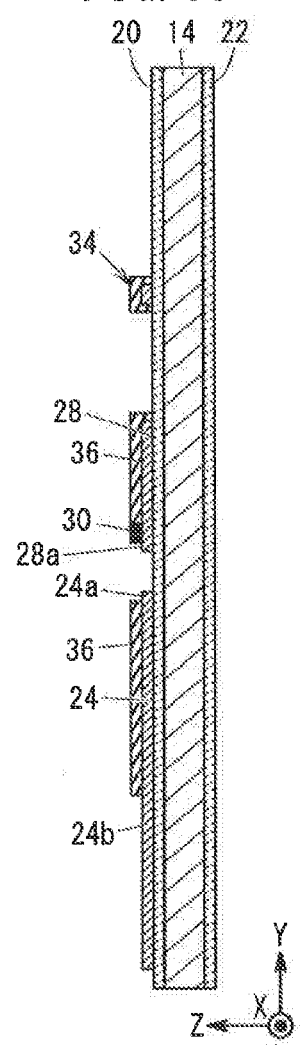
FIG. 6C is a sectional end view taken along a line VIC-VIC indicated by arrows in FIG. 6A.
Figure 6B:
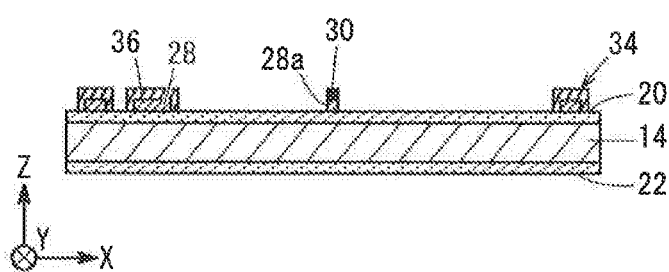
FIG. 6B is a sectional end view taken along a line VIB-VIB indicated by arrows in FIG. 6A.

Next, one surface of the first substrate 14 is covered with a lithium cobaltate membrane by radio frequency spattering (RF spattering), and thereafter, the entire photoresist is removed. As a result, as shown in FIGS. 6A to 6C, the positive electrode active material 30 made up of the lithium cobaltate membrane is formed on the connector portion 28a of the positive electrode collector 28. For the purpose of improving the activity of the positive electrode active material 30, annealing treatment for enhancing the crystallinity of the positive electrode active material 30 may be applied, or the membrane thickness or the shape pattern of the positive electrode active material 30 may be changed.

Next the one surface of the first substrate 14 is covered with a photoresist, and a photolithography process is performed. In the photolithography process, the photoresist on a portion where the negative electrode active material 26 should be formed is removed. As a result, only the portion of the connector portion 24a of the negative electrode collector 24 where the negative electrode active material 26 should be formed is exposed.

Next, the one surface of the first substrate 14 is covered with a silicon membrane by RF spattering, and thereafter, the entire photoresist is removed. As a result, as shown in FIGS. 7A to 7D, the negative electrode active material 26 made up of a silicon membrane is formed on the connector portion 24a of the negative electrode collector 24.

Next the one surface of the first substrate 14 is covered with a photoresist, and a photolithography process is performed. In the photolithography process, the photoresist on portions where the first pillar precursor 52 and the first spacer precursor 56 should be formed is removed. As a result, the second base portions 32b and the second spacer layer 34b, and only the transverse sections of the negative electrode collector 24 and the positive electrode collector 28 are exposed. In this regard, the thickness of photoresist should be determined to have a value which is about twice to 10 times as large as desired heights of the first pillar precursor 52 and the first spacer precursor 56.

Figure 10A:
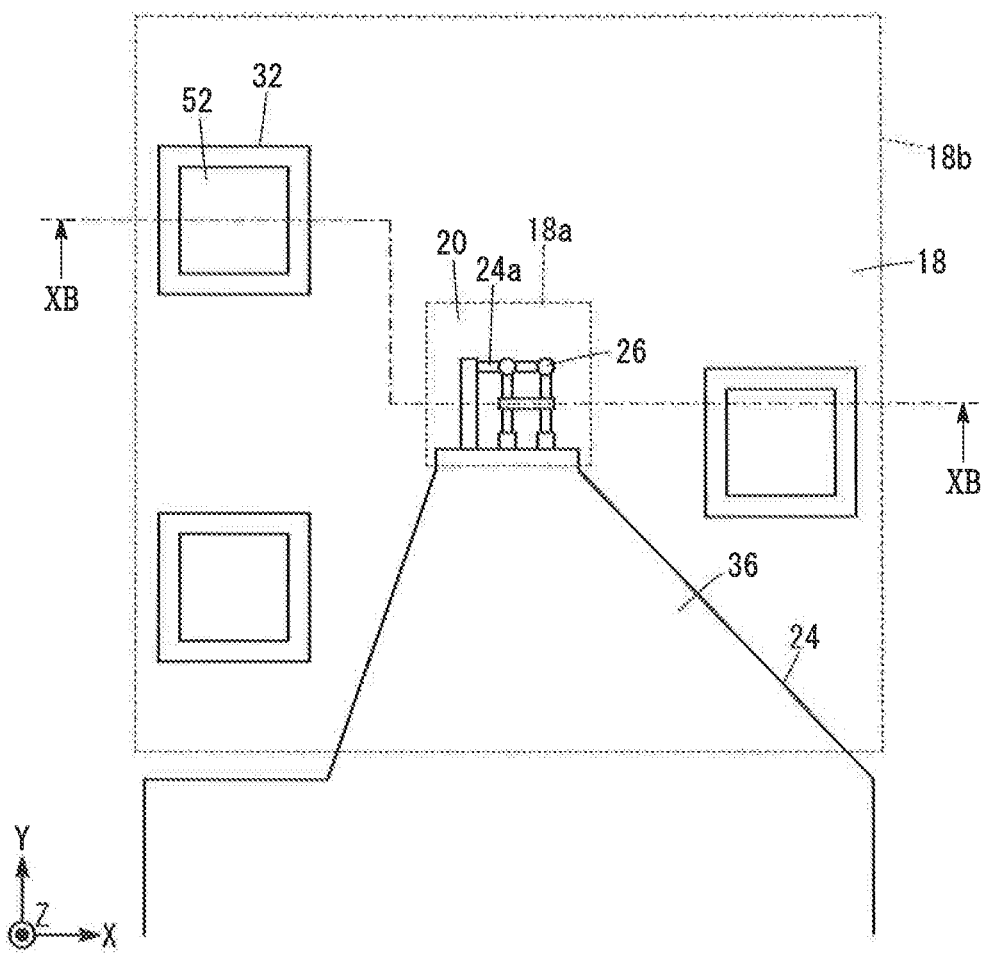
FIG. 10A is an enlarged view showing an area around the first pillar precursor shown by an arrow XA in FIG. 9A.

Next, using the PVD method, the one surface of the first substrate 14 is covered with a chromium membrane, and then, covered with a gold membrane. At the time of forming the membranes, using a membrane quantity measuring instrument as an accessory device of the PVD apparatus, in-situ monitoring of the membrane quantity (thickness) is conducted, and the deposited membrane thickness is controlled. In this manner, the membrane thickness control in the order of several nanometers can be performed. Thereafter, the entire photoresist is removed. Consequently, as shown in FIGS. 8A to 8D, the first pillar precursors 52 and the first spacer precursor 56 each comprising a stack body of the chromium membrane and the gold membrane are formed on the transmission membrane 20 of the first substrate 14. As shown in FIG. 10A in an enlarged manner, the area of the surface at one end side in the height direction of the first pillar precursor 52 may be slightly smaller than the area of the pillar joint portion 32. In this case, it becomes possible to form the first pillar precursor 52 on the pillar joint portion 32 further reliably.

Next, on the other surface of the first substrate 14, the covering membrane 22 is covered with a photoresist, and a photolithography process is performed. As a result, the photoresist is removed to expose part of the covering membrane 22 provided on a portion where the through hole 18 should be formed in the first substrate 14.

Next, a dry etching process is carried out using the photoresist as a mask. As a result, only the part of the covering membrane 22 exposed from the photoresist is removed from the first substrate 14. In this manner, after removing the part of the covering membrane 22 provided on the portion of the first substrate 14 where the through hole 18 should be formed in the first substrate 14, the entire photoresist is removed.

Next, as shown in FIGS. 9A to 9C, and FIGS. 10A and 10B, a wet etching process (through hole etching) is applied to the other surface of the first substrate 14 to thereby form the through hole 18. In this manner, the through hole 18 is formed in the first substrate 14. The through hole 18 is covered with the transmission membrane 20, from the one surface side of the first substrate 14. The one surface of the first substrate 14 may be covered with an alkali-resistant surface protection layer (not shown) before performing the wet etching process. In this case, the one surface of the first substrate 14 can be protected by the alkali-resistant surface protection layer. Further, the alkali-resistant surface protection layer should be removed by dry etching or removing liquid after forming the through hole 18 as described above.

Figure 10B:
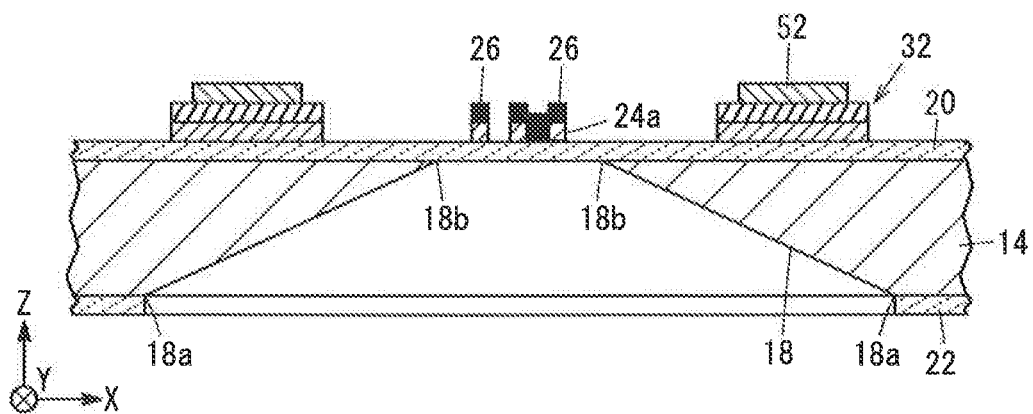
FIG. 10B is a sectional end view taken along a line XB-XB indicated by arrows in FIG. 10A.

As shown in FIGS. 10A and 10B in an enlarged manner, the first pillar precursors 52 are provided between the edge portion 18a of the through hole 18 of the other surface of the first substrate 14 and the edge portion 18b of the through hole 18 of the one surface of the first substrate 14. Further, in the surface of the first substrate 14, the first spacer precursor 56 is provided outside the edge portion 18a of the through hole 18.

Figure 11A:
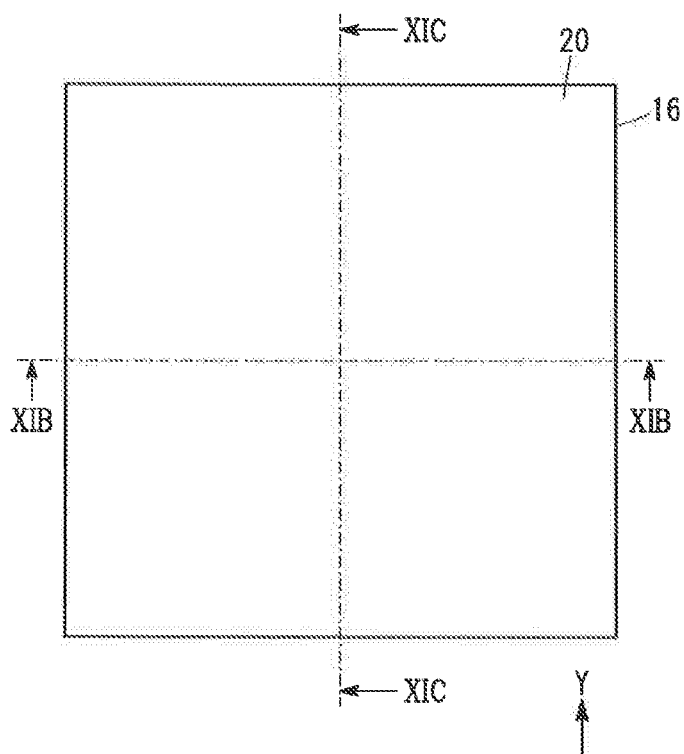
FIG. 11A is a plan view showing a transmission membrane of a second substrate having the transmission membrane on one surface and a covering membrane on the other surface.
Figure 11C:
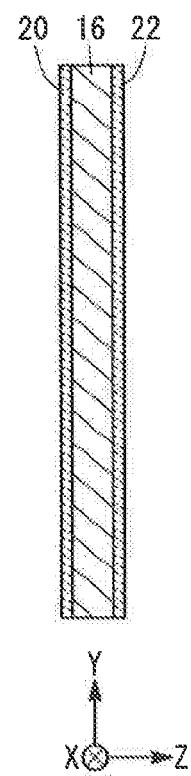
FIG. 11C is a cross sectional view taken along a line XIC-XIC indicated by arrows in FIG. 11A.
Figure 11B:
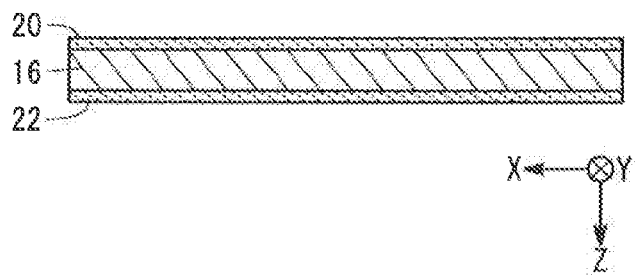
FIG. 11B is a cross sectional view taken along a line XIB-XIB indicated by arrows in FIG. 11A.

Also on the second substrate 16, as shown in FIGS. 11A to 11C, in the same manner as in the case of the first substrate 14, the transmission membrane 20 and the covering membrane 22 are provided. Next, the one surface of the second substrate 16 is covered with a photoresist, and a photolithography process is performed. As a result, the photoresist of portions where the second pillar precursors 54 and the second spacer precursor 58 should be formed is removed, and the transmission membrane 20 is exposed from the portions. In this regard, the thickness of the photoresist should be determined to have a value which is about twice to 10 times as large as desired heights of the second pillar precursor 54 and the second spacer precursor 58.

Next, using the PVD method, the one surface of the second substrate 16 is covered with a chromium membrane, and then, covered with a gold membrane. At the time of forming the membranes, using a membrane quantity measuring instrument as an accessory device of the PVD apparatus, in-situ monitoring of the membrane quantity (thickness) is conducted, and the deposited membrane thickness is controlled. In this manner, the membrane thickness control in the order of several nanometers can be performed. Thereafter, the entire photoresist is removed. Consequently, as shown in FIGS. 12A to 12C, the second pillar precursors 54 and the second spacer precursor 58 each comprising a stack body of the chromium membrane and the gold membrane are formed on the transmission membrane 20 of the second substrate 16.

Next, the one surface of the second substrate 16 is covered with a photoresist, and a photolithography process is performed. As a result, the photoresist is partly removed so as to expose part of the transmission membrane 20 provided on portions where the injection ports 42 should be formed in the second substrate 16.

Figure 13A:
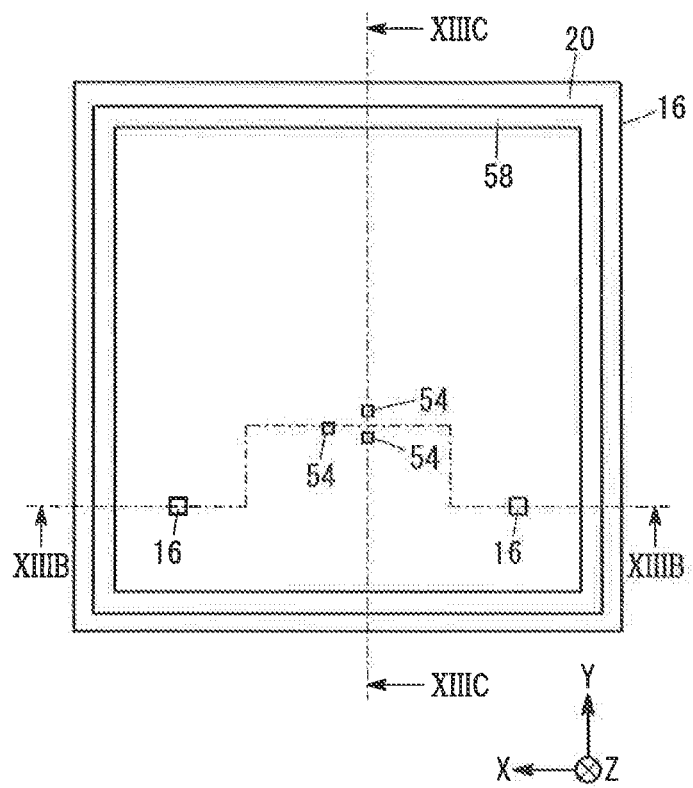
FIG. 13A is a plan view showing a state where a transmission membrane has been removed at portions where injection ports should be formed in the second substrate of FIG. 12A.
Figure 13C:
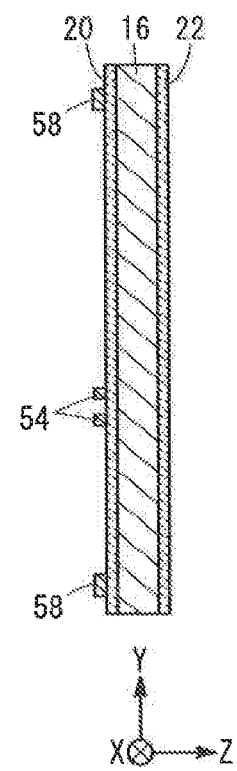
FIG. 13C is a sectional end view taken along a line XIIIC-XIIIC indicated by arrows in FIG. 13A.
Figure 13B:
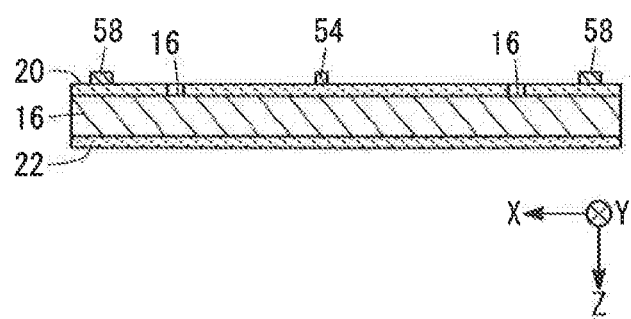
FIG. 13B is a sectional end view taken along a line XIIIB-XIIIB indicated by arrows in FIG. 13A.

Next, a dry etching process is carried out using the photoresist as a mask. As a result, only the part of the transmission membrane 20 provided on the portions where the injection ports 42 should be formed is removed. Thereafter, the entire photoresist is removed. In this manner, as shown in FIGS. 13A to 13C, only the part of the transmission membrane 20 provided on the portions of the second substrate 16 where the injection ports 42 should be formed is removed, and the portions of the second substrate 16 are exposed.

Next, the covering membrane 22 on the other surface of the second substrate 16 is covered with a photoresist, and a photolithography process is performed. As a result, the photoresist is partly removed to expose part of the covering membrane 22 provided on portions where the through hole 40 and the injection ports 42 of the second substrate 16 should be formed.

Figure 14A:
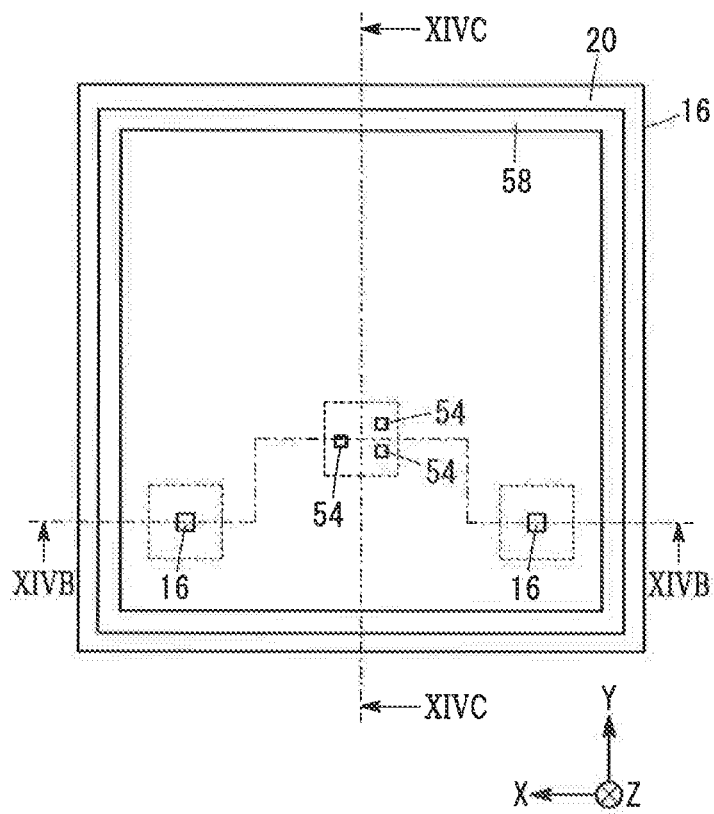
FIG. 14A is a plan view showing a state where a covering member has been removed at portions where a through hole and the injection ports should be formed in the second substrate of FIG. 13A.
Figure 14C:
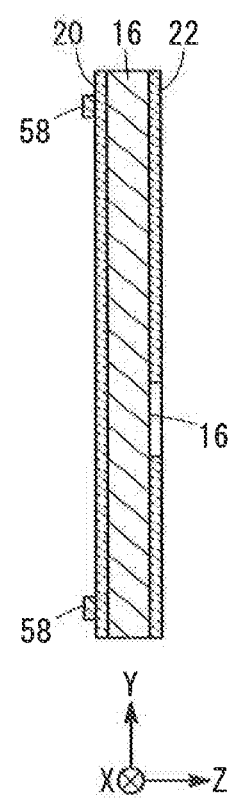
FIG. 14C is a sectional end view taken along a line XIVC-XIVC indicated by arrows in FIG. 14A.
Figure 14B:
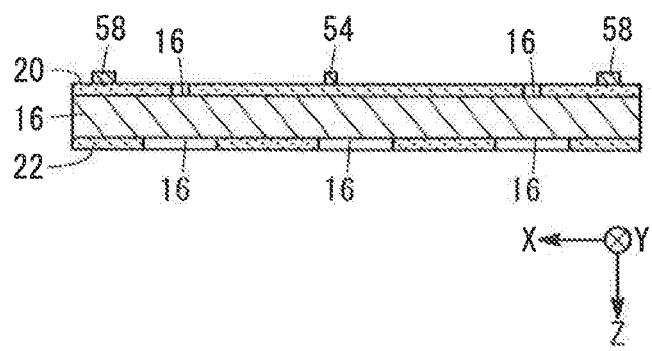
FIG. 14B is a sectional end view taken along a line XIVB-XIVB indicated by arrows in FIG. 14A.

Next, a dry etching process is carried out using the photoresist as a mask. As a result, only the part of the covering membrane 22 provided on the portions where through hole 40 and the injection ports 42 should be formed is removed. Thereafter, the entire photoresist is removed. In this manner, as shown in FIGS. 14A to 14C, only the part of the covering membrane 22 provided on the portions of the second substrate 16 where the through hole 40 and the injection ports 42 should be formed are removed, and the portions of the second substrate 16 are exposed.

Next, as shown in FIGS. 15A to 15C, 16A, 16B, a wet etching process (through hole etching) is applied to the second substrate 16 to thereby form the through hole 40 and the injection ports 42. As a result, the through hole 40 covered with the transmission membrane 20, from the one surface side of the second substrate 16 is formed in the second substrate 16. Further, the injection ports 42 exposed from the transmission membrane 20 and the covering membrane 22 are formed in the second substrate 16.

As shown in FIGS. 16A and 16B in an enlarged manner, the second pillar precursors 54 are arranged between the edge portion 40a of the through hole 40 of the other surface of the second substrate 16 and the edge portion 40b of the through hole 40 of the one surface of the second substrate 16. Further, in the surface of the second substrate 16, the second spacer precursor 58 is arranged outside the edge portion 40a of the through hole 40.

A pair of the first pillar precursor 52 and the second pillar precursor 54 which correspond to each other should be provided at respective positions of the first substrate 14 and the second substrate 16 where the pillar 46 should be formed. That is, in the embodiment of the present invention, as shown in FIGS. 10A and 16A, though three pairs of the first pillar precursors 52 and the second pillar precursors 54 are provided, the present invention is not limited in this respect as long as at least one pair of the first pillar precursor 52 and the second pillar precursor 54 are provided.

After the above series of processes, the first substrate 14 and the second substrate 16 having the various constituent elements are overlapped with each other, and the first pillar precursor 52 and the second pillar precursor 54 which correspond to each other are brought into contact with each other, and the first spacer precursor 56 and the second spacer precursor 58 which correspond to each other are brought into contact with each other. At this time, for example, an adjustment is made in a manner that the edge portions 18b, 40b of the through holes 18, 40 provided on the one surface side of the first substrate 14 and the second substrate 16 are overlapped and in alignment with each other in a plan view. Thus, the first substrate 14 and the second substrate 16 can be positioned easily and highly accurately in a manner that the through holes 18, 40 are arranged face-to-face with each other across the transmission membranes 20 to thereby form the observation window 50.

In order to suppress variation in the contact area between the first spacer precursor 56 and the second spacer precursor 58 that are placed into contact with each other as described above, preferably, the protruding end surfaces (bonding surfaces) of the first spacer precursor 56 and the second spacer precursor 58 have different lengths in the lateral direction. In the structure, when a load is applied to the first spacer precursor 56 and the second spacer precursor 58 so as to be placed in contact, as described later, it is possible to suppress the occurrence of pressure variation, and improve the bonding uniformity by the spacer 48.

In the embodiment where the contact surfaces (bonding surfaces) of the first pillar precursor 52 and the second pillar precursor 54 are made of gold, and the contact surfaces (bonding surfaces) of the first spacer precursor 56 and the second spacer precursor 58 are made of gold, solid state bonding should be performed as follows: Specifically, the bonding surfaces of the first pillar precursor 52 and the second pillar precursor 54 are brought into contact with (abutment against) each other, and the bonding surfaces of the first spacer precursor 56 and the second spacer precursor 58 are brought into contact with (abutment against) each other. In this state, a pressure load in a range of 0.2 to 2.0 kgf, preferably 1.0 kgf, per the unit bonding area of 1 mm$^2$ should be applied to the first pillar precursor 52 and the second pillar precursor 54, and the first spacer precursor 56 and the second spacer precursor 58, e.g., at temperature in a range of 300 to 400 C.°, preferably at temperature of 300 C.° for 15 to 60 minutes. In this manner, as shown in FIGS. 17A to 17C, the first pillar precursor 52 and the second pillar precursor 54 are bonded together firmly to obtain the pillar 46, and the first spacer precursor 56 and the second spacer precursor 58 are bonded together firmly to form the spacer 48.

In the case where each of the above bonding surfaces is made of aluminum, the same load as described above should be applied at temperature in a range of 400 to 450° C., preferably at temperature of 400° C., for the same time period as described above. Alternatively, in the case where each of the bonding surfaces are made of copper, the same load as described above should be applied at temperature in a range of 350 to 450° C., preferably at temperature of 350° C., for the same time period as described above.

Further, in the case where each of the bonding surfaces is made of the above-described inorganic material, the bonding surfaces should be activated before formation of the overlapping portion 12. Activation of such boding surfaces can be performed using existing devices such as a room-temperature wafer bonder "BOND MEISTER" (product name) of Mitsubishi Heavy Industries, Ltd., a surface activation wafer bonding kit (Model type: WP-100) of PMT Corporation, or the like.

More specifically, sputter etching using ion beams, plasma, etc. may be applied to each of the bonding surfaces in a vacuum chamber at room temperature under high vacuum. In this manner, it is possible to remove an oxide film and absorption films comprising water, organic material, etc., formed on the bonding surfaces to thereby expose atoms having bonds, i.e., activate the bonding surfaces. If the bonding surfaces activated in this manner are brought into contact with each other, a bonding force is generated between the bonding surfaces. As a result, it is possible to obtain the pillar 46 by firmly bonding the first pillar precursor 52 and the second pillar precursor 54, and obtain the spacer 48 by firmly bonding the first spacer precursor 56 and the second spacer precursor 58. The bonding conditions in this process should be determined appropriately based on the material, shape, or the like of the first pillar precursor 52 and the second pillar precursor 54, and the first spacer precursor 56 and the second spacer precursor 58.

By forming the pillar 46 and the spacer 48 as described above, in the state where the substrates 14, 16 jointly form the overlapping portion 12, the substrates 14, 16 are joined together. Further, the transmission membranes 20 of the observation window 50 are kept spaced from each other by a predetermined distance in correspondence with the heights of the pillar 46 and the pillar joint portion 32. Further, the transmission membranes 20 of the substrates 14, 16 are kept spaced from each other by a predetermined distance in correspondence with the heights of the spacer 48 and the spacer joint portion 34.

This pillar 46 is formed without melting the first pillar precursor 52 and the second pillar precursor 54. Therefore, the height of the pillar 46 becomes substantially equal to the sum of the heights of the first pillar precursor 52 and the second pillar precursor 54. Likewise, the height of the spacer 48 becomes substantially equal to the sum of the heights of the first spacer precursor 56 and the second spacer precursor 58. That is, by adjusting the heights of the first pillar precursor 52, the second pillar precursor 54, the first spacer precursor 56, and the second spacer precursor 58, it is possible to make settings of the distance between the transmission membranes 20 of the substrates 14, 16 easily.

Figure 18A:
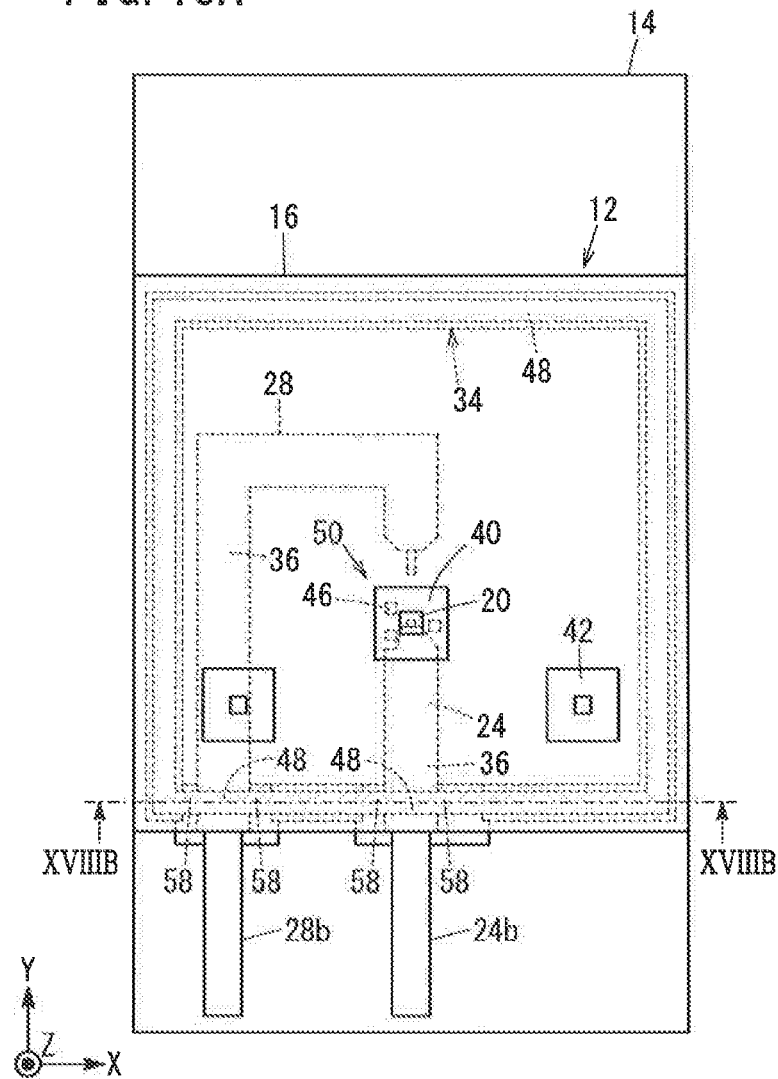
FIG. 18A is a plan view showing a state where a portion which is not sealed by a spacer in the overlapping portion in FIG. 17A is sealed by a seal member.
Figure 18B:
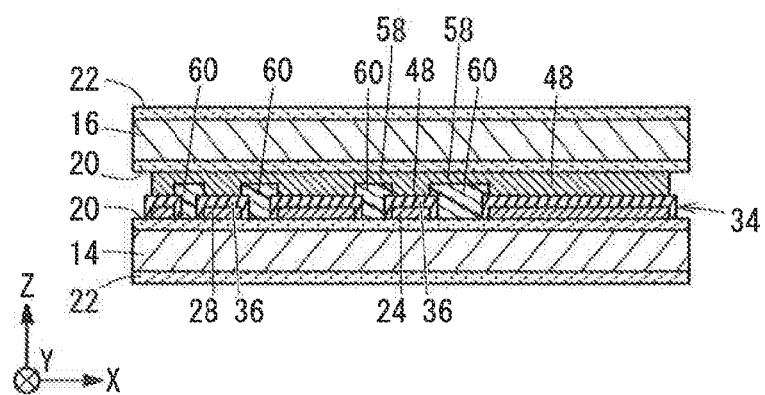
FIG. 18B is a sectional end view taken along a line XVIIIB-XVIIIB indicated by arrows in FIG. 18A.

Then, the electrolytic solution 38 (see FIGS. 1A to 1C) is injected from the injection ports 42 shown in FIGS. 18A and 18B, and a space between the first substrate 14 and the second substrate 16 is filled with the electrolytic solution 38. Thereafter, the seal member 60 is provided adjacent to the transverse section on the first substrate 14. That is, the spacer 48 is not formed in a portion where the first spacer precursor 56 is not formed, and a space is formed between the second spacer precursor 58 and the transmission membrane 20 of the first substrate 14. By providing the seal member 60 in this space, it is possible to seal the outer circumference of the overlapping portion 12.

Stated otherwise, by providing the spacer 48 to have the above shape and layout configuration, it is possible to seal the major part of the outer circumference of the overlapping portion 12 by the spacer 48. Therefore, the seal member 60 is provided only in the remaining portion which is not sealed by the spacer 48. Further, by closing the injection ports 42 by the seal member 44, it is possible to easily form a liquid tight space in the overlapping portion 12. As a result, the negative electrode active material 26 provided between the transmission membranes 20 of the observation window 50 and the positive electrode active material 30 provided in the overlapping portion 12 separately contact the electrolytic solution 38, to form a lithium ion cell. That is, with the simple processes, the analytical cell 10 can be obtained at low cost.

In the above structure, in the overlapping portion 12 of the analytical cell 10, the distance between the substrates 14, 16 is maintained by the spacer 48, and the distance between the transmission membranes 20 of the observation window 50 is maintained by the pillar 46. Since the pillar 46 is positioned between the first position P1 and the second position P2 in the overlapping portion 12, the pillar 46 is provided close to the observation window 50. Therefore, the distance between the substrates 14, 16 of the overlapping portion 12, in particular, the distance between the transmission membranes 20 of the observation window 50 can be adjusted highly accurately. Further, even in the case where an external force is applied to the analytical cell 10, it is possible to suppress occurrence of changes in the distance between the transmission membranes 20 effectively.

Therefore, in this analytical cell 10 wherein constituent elements such as the negative electrode active material 26 is provided between the transmission membranes 20 of the observation window 50, the distance between the transmission membranes 20 can be adjusted to be reduced to an extent that only a slight gap is formed between the constituent elements and the transmission membrane 20 of the second substrate 16, and the distance can be maintained. That is, in order to obtain a desired resolution in the TEM observation, etc., it is possible to reduce the distance between the transmission membranes 20 of the observation window 50, and prevent the negative electrode active material 26, etc. from being pressed between the transmission membranes 20. As a result, it becomes possible to improve the observation accuracy without degrading the durability of the analytical cell 10.

Further, in this analytical cell 10, the pillar 46c is provided in the vicinity of the space between the negative electrode active material 26 and the positive electrode active material 30 which face each other, in the overlapping portion 12. In the structure, the distance between the transmission membranes 20 in the vicinity of the negative electrode active material 26 and the positive electrode active material 30 can be maintained suitably. Thus, it is possible to suppress contact of the transmission membranes 20 with the negative electrode active material 26 and the positive electrode active material 30 effectively. Further, even in the case where an external force is applied to the analytical cell 10, since it is possible to secure contact between the electrolytic solution 38 and each of the negative electrode active material 26 and the positive electrode active material 30, the electrode reactions occur suitably, and improvement in the observation accuracy is achieved.

Further, in the presence of the pillars 46 and the spacer 48 each obtained by solid state bonding, it is possible to firmly join the substrates 14, 16 together. Accordingly, even in the case where the analytical cell 10 is attached to the holder, and observation is performed using an electron microscope in a high vacuum atmosphere, it is possible to effectively suppress positional displacement between the substrates 14, 16 and occurrence of changes in the distance between the transmission membranes 20 of the observation window 50.

The present invention is not limited to the embodiments described above, and various modifications can be made without deviating from the scope of the present invention.

For example, in the analytical cell 10 according to the above embodiment of the present invention, the solid state joint of the first pillar precursor 52 and the second pillar precursor 54 form the pillar 46 to firmly join the transmission membranes 20 of the observation window 50 together. However, the present invention is not limited in this respect. For example, the pillar 46 may comprise a stack body formed only by bringing the first pillar precursor 52 and the second pillar precursor 54 in contact with each other, whereby the analytical cell 10 may be obtained easily and efficiently.

Further, in the analytical cell 10 according to the above embodiment, the pillar 46 and the spacer 48 are formed respectively on the pillar joint portion 32 and the spacer joint portion 34 formed on the transmission membrane 20 of the first substrate 14. However, the present invention is not limited in this respect. The pillar joint portion 32 may be provided on both of the transmission membranes 20 of the first substrate 14 and the second substrate 16. Alternatively, the pillar joint portion 32 may be provided on the transmission membrane 20 of the second substrate 16, instead of the first substrate 14. Further, the pillar 46 may be formed in the overlapping portion 12 without providing the pillar joint portion 32. The same applies to the spacer joint portion 34.

Further, in the analytical cell 10 according to the above embodiment, among the negative electrode active material 26 and the positive electrode active material 30, only the negative electrode active material 26 is provided between the transmission membranes 20 of the observation window 50. However, the present invention is not limited in this respect. Both of the negative electrode active material 26 and the positive electrode active material 30 or only the positive electrode active material 30 may be provided between the transmission membranes 20 of the observation window 50. Also in this case, the same working effects and advantages as in the case of the analytical cell 10 according to the above embodiment are obtained.

Furthermore, in the case where the analytical cell 10 or the like of the above embodiment is not the lithium-ion secondary cell but the nickel-hydrogen cell, for example, a positive electrode of nickel hydroxide, a negative electrode of any of various hydrogen storing alloys, and an electrolytic solution of an aqueous potassium hydroxide solution KOH (aq) may be used. Alternatively, in the case where the analytical cell 10 is the alkaline-manganese cell, for example, a positive electrode of manganese dioxide/graphite, a negative electrode of zinc, and an electrolytic solution of KOH(aq) may be used.

Further, the analytical cell 10 can be used in an analysis not only in the TEM but also in any general analytical instrument using an electron beam.

Embodiment Example

Using the above steps, a test specimen of the analytical cell 10 according to the embodiment example was produced. Specifically, as the first substrate 14, a silicon substrate having the width of 4.0 mm, the depth of 4.0 mm, and the thickness of 200 µm was adopted. A through hole 18 having the width of 60 µm and the depth of 60 µm was formed in the silicon substrate. Further, as the transmission membrane 20, a silicon nitride membrane having the thickness of 80 nm was adopted. As the negative electrode collector 24 and the positive electrode collector 28, tungsten membranes having the thickness of 120 nm were adopted.

The connector portion 24a of the negative electrode collector 24 had a shape shown in FIG. 5D. As the negative electrode active material 26, silicon having a shape shown in FIG. 7D was adopted. As the insulating membrane 36, a silicon nitride membrane having the thickness of 160 nm was adopted. The layout configuration, the number, and the shape of the first pillar precursors 52 were set as shown in FIG. 10A.

The pillar joint portion 32 was formed by covering a first base portion 32a (thickness of 120 nm) with a second base portion 32b (thickness of 160 nm). The first base portion 32a comprises a tungsten membrane formed in the same manner as the negative electrode collector 24 and the positive electrode collector 28. The second base portion 32b comprises a silicon nitride membrane formed in the same manner as the insulating membrane 36. That is, the thickness of the pillar joint portion 32 was 280 nm. Further, the surface of the pillar joint portion 32 at one end in the height direction was formed into a square shape with the side length of 80 µm.

The first pillar precursor 52 was a stack body including a chromium membrane formed on the pillar joint portion 32 and a gold membrane formed on the chromium membrane. The thickness of this chromium membrane was 50 nm, and the thickness of the gold membrane was 200 nm. Therefore, the height of the first pillar precursor 52 was 250 nm. Further, the surface of the first pillar precursor 52 at one end in the height direction was formed into a square shape with the side length of 60 µm.

The spacer joint portion 34 was formed in the same manner as the pillar joint portion 32. The first spacer precursor 56 is formed on the spacer joint portion 34 in the same manner as the first pillar precursor 52. Further, each of the sides of the first spacer precursor 56 in the depth direction and in the width direction had the length of 3.75 mm. The surface (bonding surface) of the first spacer precursor 56 at one end in the height direction had the lateral length of 0.1 mm. That is, the surface area of the bonding surface of the first spacer precursor 56 was 1.25 mm$^2$.

Further, as the second substrate 16, a silicon substrate having the width of 4.0 mm, the depth of 4.0 mm, and the thickness of 200 µm was adopted. A through hole 40 having the same shape as the through hole 18 of the first substrate 14, and injection ports 42 each having the width of 500 µm and the depth of 500 µm were formed in the silicon substrate. The layout configuration, the number, and the shape of the second pillar precursors 54 were set as shown in FIG. 16A.

The second pillar precursor 54 was a stack body including a chromium membrane formed on the transmission membrane 20 and a gold membrane formed on the chromium membrane. The thickness of this chromium membrane was 50 nm, and the thickness of the gold membrane was 400 nm. Therefore, the height of the second pillar precursor 54 was 450 nm. Further, the surface (bonding surface) of the first pillar precursor 52 at one end in the height direction was formed into a square shape with the side length of 60 μm.

The second spacer precursor 58 was formed in the same manner as the second pillar precursor 54. Further, each of the sides of the second spacer precursor 58 in the depth direction and in the width direction had the length of 3.8 mm. The surface (bonding surface) of the second spacer precursor 58 at the other end in the height direction had the lateral length of 0.15 mm. That is, the surface area of the bonding surface of the second spacer precursor 58 was 2.19 mm².

Therefore, the bonding area for bonding the first pillar precursor 52 and the second pillar precursor 54 by solid state bonding is 0.0108 mm² (60 μm×60 μm×3=0.0108 mm²). Further, since the total value of the heights of the first pillar precursor 52 and the second pillar precursor 54 is 700 nm, the preset value of the height of the pillar 46 is 700 nm.

The bonding area for bonding the first spacer precursor 56 and the second spacer precursor 58 by solid state bonding was 1.25 mm². Further, since the total value of the lengths of the first spacer precursor 56 and the second spacer precursor 58 was 700 nm, the preset value of the height of the spacer 48 was 700 nm.

That is, in the analytical cell 10 according to the embodiment example, 980 nm, which was the total value of the heights of the pillar 46 (spacer 48) and the pillar joint portion 32 (spacer joint portion 34), was used as a target setting value of the distance between the transmission membranes 20 of the substrates 14, 16.

Then, the first substrate 14 and the second substrate 16 were overlapped with each other, and positioned as described above, so that the bonding surfaces of the first pillar precursor 52 and the second pillar precursor 54 were brought into contact with each other, and the bonding surfaces of the first spacer precursor 56 and the second spacer precursor 58 were also brought into contact with each other. Then, solid state bonding was performed by applying a load of 1000 g at 350° C. for 30 minutes to thereby join the substrates 14, 16 together, whereby the overlapping portion 12 was formed.

In this overlapping portion 12, it was confirmed that the distance between the transmission membranes 20 of the substrates 14, 16 was substantially 1000 nm. That is, as a result of obtaining the overlapping portion 12 as described above, the distance between the transmission membranes 20 of the substrates 14, 16, in particular, the distance between the transmission membranes 20 of the observation window 50 was able to be set at substantially the target setting value.

Next, the electrolytic solution 38 was prepared by dissolving $LiPF_6$, at the concentration of 1M, in a solution obtained by mixing EC and EMC at the ratios of 3:7. The resulting electrolytic solution 38 was injected into the overlapping portion 12 through the injection ports 42. Thereafter, a seal member 60 made of an epoxy resin was provided to seal the area around the transverse section of the overlapping portion 12. Further, the injection ports 42 were closed by the seal members 44 of epoxy resin. In this manner, in the overlapping portion 12, the negative electrode active material 26 and the positive electrode active material 30 separately contact the electrolytic solution 38, and a test specimen of the analytical cell 10, which forms a lithium ion cell, according to the embodiment example was obtained.

In the test specimen of this analytical cell 10, it was confirmed that the distance between the transmission membranes 20 of the observation window 50 was about 1000 nm, and no damage was caused in any of the transmission membranes 20 and the negative electrode active material 26.

Comparative Example

A test specimen of an analytical cell according to a comparative example was prepared by the same steps as those for the test specimen of the analytical cell 10 according to the embodiment of the present invention, except that no pillar 46 was formed in the comparative example. In the test specimen of the analytical cell according to the comparative example, it was confirmed that, when substrates 14, 16 were stacked together, and a load was applied for solid state bonding of the first spacer precursor 56 and the second spacer precursor 58, damage was caused in the transmission membranes 20 of the observation window 50. Therefore, solid state bonding was cancelled, and the overlapped first and second substrates 14, 16 were separated away from each other. One surface of each of the first substrate 14 and the second substrate 16 was observed using an optical microscope. As a result, part of the transmission membrane 20 peeled off from the second substrate 16 was adhered to the negative electrode collector 24 of the first substrate 14, and part of the transmission membrane 20 covering the through hole 40 of the second substrate 16 was lost.

As described above, since the analytical cell 10 according to the embodiment of the present invention has the pillars 46 and the spacer 48, it is possible to highly accurately adjust and maintain the distance between the transmission membranes 20 of the observation window 50. Further, it is possible to avoid damage to the constituent elements caused by being pressed between the transmission membranes 20. Therefore, it is possible to reduce the distance between the transmission membranes 20 of the observation window 50, and improve the observation accuracy without degrading the durability of the analytical cell 10.

What is claimed is:

1. An analytical cell comprising substrates overlapped with each other to form an overlapping portion, a negative electrode active material and a positive electrode active material being provided in the overlapping portion and separately contacting electrolytic solution, an observation window for transmission of an electron beam in an overlapping direction of the overlapping portion being provided in the overlapping portion, wherein the substrates have respective through holes extending through the substrates in a thickness direction thereof, the substrates each having main surfaces on both sides thereof in the thickness direction;

each of the through holes has a shape that is tapered from an outer surface of the main surfaces that faces to outside of the overlapping portion, toward an inner surface of the main surfaces that faces to inside of the overlapping portion, and the through holes are covered with respective transmission membranes from a side of the inner surface, the transmission membranes each having an electron beam permeability;

the observation window is formed between the through holes facing each other across the transmission membranes;

at least one of the negative electrode active material and the positive electrode active material is formed between the transmission membranes of the observation window;

in the overlapping portion, at least one pillar configured to maintain a distance between the transmission membranes of the observation window is provided between a first position and a second position, the first position being a position where edge portions of the through holes of the outer surfaces of the substrates are disposed face-to-face with each other in the overlapping direction, the second position being a position where edge portions of the through holes of the inner surfaces of the substrates are disposed face-to-face with each other in the overlapping direction, and at least one spacer configured to maintain a distance between the substrates is provided at a position shifted from the first position toward a circumferential edge portion of the overlapping portion; and a negative electrode collector and a positive electrode collector extend from inside of the overlapping portion and protrude outside the overlapping portion, and the negative electrode collector and the positive electrode collector are electrically connected respectively to the negative electrode active material and the positive electrode active material inside the overlapping portion.

2. The analytical cell according to claim 1, wherein the pillar comprises at least three pillars that are not on a same straight line.

3. The analytical cell according to claim 1, wherein the pillar comprises a pair of pillars that face each other across the observation window.

4. The analytical cell according to claim 1, wherein the pillar comprises one pillar provided in a vicinity of a space between the negative electrode active material and the positive electrode active material that face each other, in the overlapping portion.

* * * * *